United States Patent
Yoshida

(10) Patent No.: US 7,550,463 B2
(45) Date of Patent: Jun. 23, 2009

(54) CARBAMOYLPYRIDONE DERIVATIVES HAVING INHIBITORY ACTIVITY AGAINST HIV INTEGRASE

(75) Inventor: Hiroshi Yoshida, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 168 days.

(21) Appl. No.: 11/662,768

(22) PCT Filed: Sep. 14, 2005

(86) PCT No.: PCT/JP2005/016904

§ 371 (c)(1),
(2), (4) Date: Mar. 14, 2007

(87) PCT Pub. No.: WO2006/030807

PCT Pub. Date: Mar. 23, 2006

(65) Prior Publication Data

US 2007/0249687 A1  Oct. 25, 2007

(30) Foreign Application Priority Data

Sep. 15, 2004   (JP) .............................. 2004-267720

(51) Int. Cl.
*A61K 31/53* (2006.01)
*A61K 31/497* (2006.01)
*C07D 251/00* (2006.01)
*C07D 417/00* (2006.01)
*C07D 417/04* (2006.01)
*C07D 413/00* (2006.01)
*C07D 401/00* (2006.01)

(52) U.S. Cl. .................. 514/242; 514/252.12; 514/341; 514/342; 514/350; 546/269.7; 546/270.4; 546/271.4; 546/272.7; 544/215

(58) Field of Classification Search ................ 546/221, 546/269.7, 270.4, 271.4, 272.7; 549/28, 549/418; 514/328, 445, 460, 242, 252.12, 514/341, 342, 350; 544/215
See application file for complete search history.

(56) References Cited

U.S. PATENT DOCUMENTS 6,645,956 B1  11/2003 Fujishita et al.

(Continued)

FOREIGN PATENT DOCUMENTS

EP  1 544 199  6/2005

(Continued)

OTHER PUBLICATIONS

Pace et. al., "The monoethyl ester of moeconic acid is an active site inhibitor of HCV NS5B RNA-dependent RNA polymerase", Biooraganic & Medicinal Chemistry Letters 14 (2004) 3257-3261.*

(Continued)

*Primary Examiner*—Janet L. Andres
*Assistant Examiner*—Binta M Robinson
(74) *Attorney, Agent, or Firm*—Wenderoth, Lind & Ponack, L.L.P.

(57) ABSTRACT

An object of the present invention provides a novel compound having the anti-viral activity, particularly, the HIV integrase inhibitory activity, and a drug containing the same, particularly, an anti-HIV drug.

There is provided a compound represented by the formula:

[Chemical formula 1]

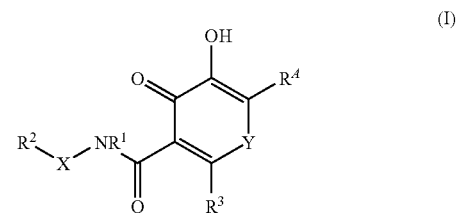

(I)

wherein,
Y is $NR^4$ ($R^4$ is hydrogen, optionally substituted lower alkyl, optionally substituted aryl, or optionally substituted aralkyl), O, S, SO, or $SO_2$;
$R^A$ is 1) a group represented by the formula: $—COR^5$ (wherein $R^5$ is a group selected from a substituent group A), or 2) a group represented by the formula:

[Chemical formula 2]

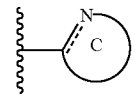

(wherein A C ring is an optionally substituted nitrogen-containing aromatic heterocycle in which, among atoms adjacent to an atom having a bond, at least one atom is an unsaturated nitrogen atom, and a broken line represents the presence or the absence of a bond);
$R^1$ is a hydrogen or lower alkyl;
X is a single bond, a hetero atom group selected from O, S, SO, $SO_2$ and NH, or lower alkylene or lower alkenylene in which the hetero atom group may intervene;
$R^2$ is a group selected from a substituent group A;
$R^3$ is hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl)
or a pharmaceutically acceptable salt thereof, or a solvate thereof.

17 Claims, No Drawings

U.S. PATENT DOCUMENTS

| | | |
|---|---|---|
| 2004/0002485 A1 | 1/2004 | Fujishita et al. |
| 2004/0110804 A1 | 6/2004 | Walker et al. |
| 2004/0229909 A1 | 11/2004 | Kiyama et al. |
| 2005/0054645 A1 | 3/2005 | Miyazaki et al. |
| 2005/0075356 A1 | 4/2005 | Di Francesco et al. |
| 2005/0176767 A1 | 8/2005 | Chan Chun Kong et al. |

FOREIGN PATENT DOCUMENTS

| | | |
|---|---|---|
| JP | 02-108668 | 4/1990 |
| JP | 02-108683 | 4/1990 |
| JP | 2004-244320 | 9/2004 |
| WO | 00/39086 | 7/2000 |
| WO | 03/016275 | 2/2003 |
| WO | 03/035076 | 5/2003 |
| WO | 2004/004657 | 1/2004 |
| WO | 2004/024693 | 3/2004 |
| WO | 2005/042524 | 5/2005 |

OTHER PUBLICATIONS

Hcaplus 138:204936.*

Hcaplus 87:14971a, 14974a.*

West, Anthony R., Solid State Chemistry and its Applications, Wiley, New York, 1988, pp. 358 & 365.*

S. Tewtrakul et al., "Flavanone and Flavonol Glycosides from the Leaves of *Thevetia peruvianna* and their HIV-1 Reverse Transcriptase and HIV-1 Integrase Inhibitory Activities", Chem. Phar. Bull, vol. 50, No. 5, pp. 630-635, May 2002.

\* cited by examiner

CARBAMOYLPYRIDONE DERIVATIVES HAVING INHIBITORY ACTIVITY AGAINST HIV INTEGRASE

This application is a U.S. national stage of International Application No. PCT/JP2005/016904 filed Sep. 14, 2005.

TECHNICAL FIELD

The present invention relates to a novel compound having the antiviral activity, more particularly, carbamoylpyridone derivatives having the inhibitory activity against HIV integrase and a pharmaceutical composition, particularly an anti-HIV agent, containing the same.

BACKGROUND ART

Among viruses, human immunodeficiency virus (HIV), a kind of retrovirus, is known to cause acquired immunodeficiency syndrome (AIDS). The therapeutic agent for AIDS is mainly selected from a group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, a multidrug combination therapy is reported to be efficient in treatment for acquired immunodeficiency syndrome (AIDS) because of the frequent emergency of the resistant mutant. Reverse transcriptase inhibitors and protease inhibitors are clinically used as an anti-HIV agent, however, agents having the same mechanism of action often exhibit cross-resistance or only the additional activity. Therefore, anti-HIV agents having the other mechanism of action are desired.

Under such the circumstance, as an anti-HIV drug of a novel mechanism, an integrase inhibitor is paid an attention (see: Patent Documents 1,2). In addition, as an anti-HIV drug having the same action, carbamoyl-substituted hydroxypyrimidinone derivatives (see: Patent Documents 3,4) and carbamoyl-substituted hydroxypyrrolidione derivatives (see: Patent Document 5) are known. In addition, there has been an application directed to carbamoyl-derivative hydroxypyridone derivatives (see: Patent Document 6, Example 8).

As other carbamoylpyridone derivatives, 5-alkoxypyridine-3-carboxamide derivatives and γ-pyrone-3-carboxamide derivatives are known, and they are a plant growth suppressing agent and a herbicide (see : Patent Document 7 to 9).

[Patent Document 1]
WO 03/0166275
[Patent Document 2]
WO 2004/024693
[Patent Document 3]
WO 03/035076
[Patent Document 4]
WO 03/035076
[Patent Document 5]
WO 2004/004657
[Patent Document 6]
Japanese Patent Application No.2003-32772
[Patent Document 7]
Japanese Patent Application Laid-Open (JP-A) No.2-108668
[Patent Document 8]
JP-A No.2-108683
[Patent Document 9]
JP-A No.2-96506

Under the above circumstance, the development of a novel integrase inhibitor has been desired.

DISCLOSURE OF INVENTION

The present inventors intensively studied and, as a result, found out that a novel carbamoylpyridone derivative has the strong HIV integrase inhibitory activity. , Further, the present inventors found out that the present compound and a drug containing the same are useful as an anti-virus drug (e.g. anti-retrovirus drug, anti-HIV drug, anti-HTLV-1 (Human T cell leukemia virus type 1) drug, anti-FIV (Feline immunodeficiency virus) drug, anti-SIV (Simian immunodeficiency virus)), particularly, an anti-HIV drug, an anti-AIDS drug, or a therapeutic for related diseases, which resulted in completion of the present invention shown below.

(1) A compound represented by the formula:

[Chemical formula 1]

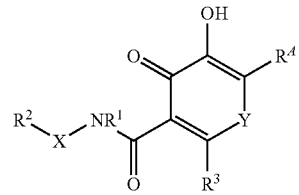

(I)

(wherein
Y is $NR^4$ (wherein $R^4$ is hydrogen, optionally substituted lower alkyl, optionally substituted aryl, or optionally substituted aralkyl), O, S, SO, or $SO_2$;

$R^4$ is 1) a group represented by the formula: $—COR^5$ (wherein $R^5$ is a group selected from a substituent group A) (substituent group A: hydrogen, hydroxy, optionally substituted lower alkyl, optionally substituted lower alkoxy, optionally substituted cycloalkyl, optionally substituted cycloalkyloxy, optionally substituted amino, optionally substituted aminooxy, optionally substituted heterocyclic group, optionally substituted heterocyclic oxy, optionally substituted aryl, optionally substituted aryloxy, optionally substituted aralkyl, optionally substituted aralkyloxy, formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, optionally -substituted arylcarbonyl)

or 2) a group represented by the formula:

[Chemical formula 2]

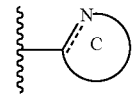

(wherein a C ring is an optionally substituted nitrogen-containing aromatic heterocycle in which, among atoms adjacent to an atom having a bond, at least one atom is an unsubstituted nitrogen atom, and a broken line represents the presence or the absence of a bond);

$R^1$ is hydrogen or lower alkyl;

X is a single bond, a hetero atom group selected from O, S, SO, $SO_2$ and NH, or lower alkylene or lower alkenylene in which the hetero atom group may intervene;

$R^2$ is a group selected from the substituent group A;

$R^3$ is hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl) or a pharmaceutically acceptable salt thereof, or a solvate thereof.

One aspect of the (1) includes the case where $R^2$ is optionally substituted aryl, and $R^3$ is hydrogen, halogen, hydroxy, optionally substituted lower alkyl, optionally substituted lower alkenyl, optionally substituted lower alkoxy, optionally substituted amino, optionally substituted cycloalkyl, optionally substituted cycloalkyl lower alkyl, optionally, substituted aryl, optionally substituted aralkyl, optionally substituted heterocyclic group, or optionally substituted heterocyclic lower alkyl.

(2) The compound according to the 1, or a pharmaceutically acceptable salt thereof, or a solvate thereof, wherein Y is $NR^4$ (wherein $R^4$ is as defined above) or O.

(3) The compound according to the 1, or a pharmaceutically acceptable salt thereof, or a solvate thereof, wherein Y is $NR^4$ (wherein $R^4$ is hydrogen, lower alkyl, phenyl or benzyl).

(4) The compound according to the 1, or a pharmaceutically acceptable salt thereof, or a solvate thereof, wherein Y is O.

(5) The compound according to the 1, or a pharmaceutically acceptable salt thereof, or a solvate thereof, wherein Y is S, SO or $SO_2$.

(6) The compound according to the 1, a pharmaceutically acceptable salt thereof, or a solvate thereof, wherein $R^A$ is —$COR^5$ (wherein $R^5$ is as defined above).

(7) The compound according to the 1, or a pharmaceutically acceptable salt thereof, or a solvate thereof, wherein $R^A$ is —$COR^5$ (wherein $R^5$ is hydrogen, hydroxy, optionally substituted lower alkyl, optionally substituted lower alkoxy, optionally substituted phenyl, optionally substituted benzyl, optionally substituted heterocyclic group or optionally substituted amino).

(8) The compound according to the 1, or a pharmaceutically acceptable salt thereof, or a solvate thereof, wherein $R^A$ is —$COR^5$ (wherein $R^5$ is hydrogen, hydroxy, lower alkyl, lower alkoxy, or optionally substituted amino).

(9) The compound according to the 1, or a pharmaceutically acceptable salt thereof, or a solvate thereof, wherein $R^A$ is a group represented by the formula:

[Chemical formula 3]

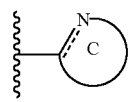

(wherein a C ring is optionally substituted nitrogen-containing aromatic heterocycle in which, among atoms adjacent to an atom having a bond, at least one atom is an unsubstituted nitrogen atom, and a broken line represents the presence or the absence of a bond).

(10) The compound according to the 1, or a pharmaceutically acceptable salt thereof, or a solvate thereof, wherein $R^A$ is an optionally substituted nitrogen-containing aromatic. heterocyclic group which is any one of the following groups.

[Chemical formula 4]

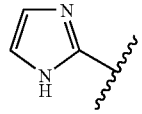 (C-1)

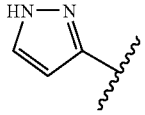 (C-2)

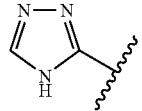 (C-3)

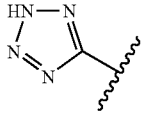 (C-4)

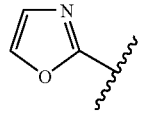 (C-5)

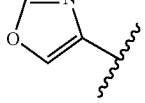 (C-6)

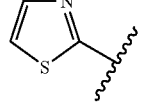 (C-7)

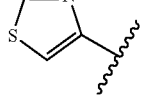 (C-8)

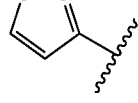 (C-9)

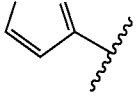 (C-10)

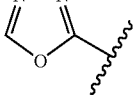 (C-11)

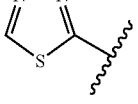 (C-12)

-continued

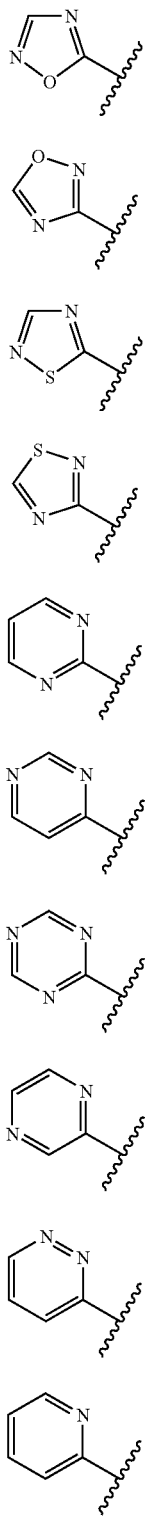

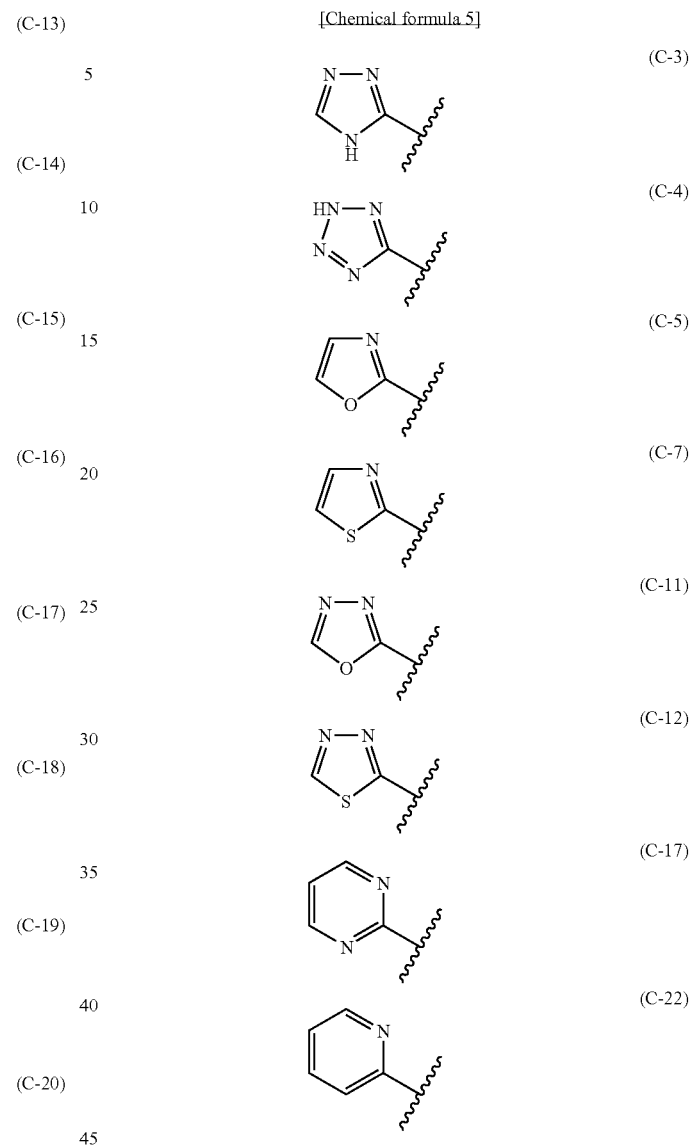

(11) The compound according to the 1, or a pharmaceutically acceptable salt thereof, or a solvate thereof, wherein $R^4$ is an optionally substituted nitrogen-containing aromatic heterocyclic group which is any one of the following groups.

(12) The compound according to the 1, or a pharmaceutically acceptable salt thereof, or a solvate thereof, wherein $R^1$ is hydrogen or methyl.

(13) The compound according to the 1, or a pharmaceutically acceptable salt thereof, or a solvate thereof, wherein X is lower alkylene or O: $R^2$ is optionally substituted phenyl.

(14) The compound according to the 1, or a pharmaceutically acceptable salt thereof, or a solvate thereof, wherein $R^3$ is hydrogen, hydroxy, optionally substituted lower alkoxy, or optionally substituted amino.

(15) The compound according to the 1, a pharmaceutically acceptable salt thereof, or a solvate thereof, wherein $R^3$ is hydrogen.

(16) The compound according to the 1, or a pharmaceutically acceptable salt thereof, or a solvate thereof, wherein Y is $NR^4$ (wherein $R^4$ is as defined above) or O; $R^1$ is hydrogen or methyl; X is lower alkylene or O; $R^2$ is optionally substituted phenyl; $R^3$ is hydrogen.

(17) The compound according to the 1, or a pharmaceutically acceptable salt thereof, or a solvate thereof, wherein Y is $NR^4$ (wherein $R^4$ is hydrogen, lower alkyl, phenyl or benzyl) or O; R¹ is hydrogen or methyl; X is methylene or O; R² is phenyl optionally substituted with halogen; R³ is hydrogen.
(18) A pharmaceutical compound, comprising a compound as defined in any one of the 1 to 17, or a pharmaceutically acceptable salt thereof, or a solvate thereof.
(19) An anti-HIV agent, comprising a compound as defined in any one of the 1 to 17, or a pharmaceutically acceptable salt thereof, or a solvate thereof.
(20) A compound represented by the formula:

[Chemical formula 45]

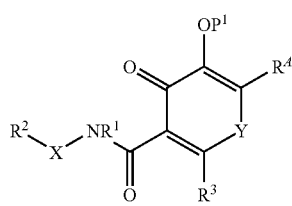

(I')

(wherein
P¹ is a hydroxy protecting group;
Y is NR⁴ (wherein R⁴ is hydrogen, optionally substituted lower alkyl, optionally substituted aryl, or optionally substituted aralkyl), O, S, SO, or SO₂;
R^A is 1) a group represented by the formula: —COR⁵ (wherein R⁵ is a group selected from a substituent group A) (substitutent group A: hydrogen, hydroxy, optionally substituted lower alkyl, optionally substituted lower alkoxy, optionally substituted cycloalkyl, optionally substituted cycloalkyloxy, optionally substituted amino, optionally substituted aminooxy, optionally substituted heterocyclic group, optionally substituted heterocyclic oxy, optionally substituted aryl, optionally substituted aryloxy, optionally substituted aralkyl, optionally substituted aralkyloxy, formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, optionally substituted arylcarbonyl or 2) a group represented by the formula:

[Chemical formula 46]

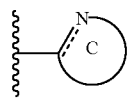

(wherein a C ring is an optionally substituted nitrogen-containing aromatic heterocycle in which, among atoms adjacent to an atom having a bond, at least one atom is an unsaturated nitrogen atom, and a broken line represents the presence or the absence of a bond);
R¹ is hydrogen or lower alkyl;
X is a single bond, a hetero atom group selected from O, S, SO, SO₂ and NH, or lower alkylene or lower alkenylene in which the hetero atom group may intervene;
R² is a group selected from the substituent group A
R³ is hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl) or a pharmaceutically acceptable salt thereof, or a solvate thereof.

(21) A compound represented by the formula:

[Chemical formula 47]

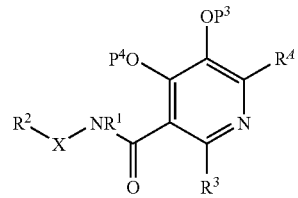

(I'')

(wherein
P³ is hydrogen or a hydroxy protecting group;
P⁴ is a hydroxy protecting group;
Y is NR⁴ (wherein R⁴ is hydrogen, optionally substituted lower alkyl, optionally substituted aryl, or optionally substituted aralkyl), O, S, SO, or SO₂;
R^A is 1) a group represented by the formula: —COR⁵ (wherein R⁵ is a group selected from a substituent group A) (substituent group A: hydrogen, hydroxy, optionally substituted lower alkyl, optionally substituted lower alkoxy, optionally substituted cycloalkyl, optionally substituted cycloalkyloxy, optionally substituted amino, optionally substituted aminooxy, optionally substituted heterocyclic group, optionally substituted heterocyclic oxy, optionally substituted aryl, optionally substituted aryloxy, optionally substituted aralkyl., optionally substituted aralkyloxy, formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, optionally substituted arylcarbonyl)
or 2) a group represented by the formula:

[Chemical formula 48]

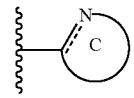

(wherein a C ring is an optionally substituted nitrogen-containing aromatic heterocycle in which, among atoms adjacent to an atom having a bond, at least one atom is an unsubstituted nitrogen atom, and a broken line represents the presence or the absence of a bond);
R¹ is hydrogen or lower alkyl;
X is a single bond, a hetero atom group selected-from O, S, SO, SO₂ and NH, or lower alkylene or lower alkenylene in which the hetero atom group may intervene;
R² is a group selected from the substituent group A;
R³ is hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl)

or a pharmaceutically acceptable salt thereof, or a solvate thereof.

EFFECT OF THE INVENTION

The present compound has the integrase inhibitory activity against a virus, particularly HIV and/or the cell proliferation inhibitory activity. Therefore, the compound is useful in preventing or treating various diseases associated with integrase, or virus infection (e.g. AIDS). Also, the present invention provides a synthesis intermediate for integrase inhibition.

BEST MODE FOR CARRYING OUT THE INVENTION

Terms used herein will be explained. Respective terms have the following meanings alone or in conjunction with other terms.

The "lower alkylene" means straight or brunched lower alkylene of a carbon number of 1 to 6, and examples include methylene, ethylene, trimethylene, propylene, tetramethylene, ethylethylene, pentamethylene and hexamethylene. Preferable is straight lower alkylene of a carbon number of 1 to 4 such as methylene, ethylene, trimethylene and tetramethylene, more preferably methylene and ethylene.

The "lower alkenylene" means a straight or branched lower alkenylene group of a carbon number of 2 to 6 having one or more double bonds in the "lower alkylene", and examples include vinylene, propenylene and butenylene. Preferable is straight lower alkenylene of a carbon number of 2 to 3, such as vinylene and propenylene.

The "alkyl" means a straight or branched alkyl group of a carbon number of 1 to 10, and examples include methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, n-decyl and the like. Preferable is lower alkyl of a carbon number of 1 to 6, and more preferable is lower alkyl of a carbon number of 1 to 4. Examples include methyl, ethyl, n-propyl, isopropyl, n-butyl, isobutyl, sec-butyl, tert-butyl, n-pentyl, isopentyl, neopentyl, tert-pentyl, n-hexyl, and isohexyl.

The "alkenyl" means straight or branched alkenyl of a carbon number of 2 to 8 having one or more double bonds in the "alkyl", and examples include vinyl, 1-propenyl, 2-propenyl, 1-butenyl, 2-butenyl, 3-butenyl, 1,3-butadienyl, 3-methyl-2-butenyl and the like. Preferable is lower alkyl of a carbon number of 2 to 6, and more preferable is lower alkyl of a carbon number of 2 to 4.

The "cycloalkyl" means a cyclic saturated hydrocarbon group of carbon number of 3 to 10, and examples include cyclopropyl, cyclobutyl, cyclopentyl, cyclohexyl, cycloheptyl, cyclooctyl and the like. Preferable is cycloalkyl of a carbon number of 3 to 6.

The "cycloalkenyl" means a cyclic non-aromatic hydrocarbon group of a carbon number of 3 to 10, and examples include cyclopropenyl (e.g. 1-cyclopropenyl), cyclobutenyl (e.g. 1-cyclobutenyl), cyclopentenyl (e.g. 1-cyclopenten-1-yl, 2-cyclopenten-1-yl, 3-cyclopenten-1-yl), cyclohexenyl (e.g. 1-cyclohexene-1-yl, 2-cyclohexen-1-yl, 3-cyclohexen-1-yl), cycloheptenyl (e.g. 1-cycloheptenyl), cyclooctenyl (e.g. 1-cyclooctenyl) and the like.

The "aryl" means a monocyclic aromatic hydrocarbon group (phenyl) and a polycyclic aromatic hydrocarbon group (e.g. 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl etc.). Preferable examples include phenyl and naphthyl (1-naphthyl, 2-naphthyl).

The "aralkyl" means the "alkyl" substituted with one to three of the aforementioned "aryl", and examples include benzyl, diphenylmethyl, triphenylmethyl, phenethyl, 1-naphthylmethyl, 2-naphthylmethyl etc.) and the like. Preferable is benzyl.

The "heterocyclic group" means "heterocycle" or "heteroaryl".

The "heterocycle" means anon-aromatic heterocyclic group (preferably 5- to 7-membered ring) having at least one of a nitrogen atom, an oxygen atom and/or a sulfur atom in a ring, and having a bond at a substitutable arbitrary position, and examples include 1-pyrrolinyl, 2-pyrrolinyl, 3-pyrrolinyl, 1-pyrrolidinyl, 2-pyrrolidinyl, 3-pyrrolidinyl, 1-imidazolynyl, 2-imidazolynyl, 4-imidazolynyl, 1-imidazolydinyl, 2-imidazolydinyl, 4-imidazolydinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, 1-piperazinyl, 2-piperazinyl, 2-morpholinyl, 3-morpholinyl, morpholino, tetrahydropyranyl and the like. The "non-aromatic-heterocyclic group" may be saturated or unsaturated as far as the group is non-aromatic.

The "heteroaryl" means a monocyclic-aromatic heterocyclic group or a fused aromatic heterocyclic group.

The monocyclic aromatic heterocyclic group means a group optionally having a bond at a substitutable arbitrary position, which is derived from a 5- to 8-membered aromatic ring optionally containing 1 to 4 of an oxygen atom, a sulfur atom and/or a nitrogen atom in a ring.

The fused aromatic heterocyclic group means a group optionally having a bond at a substitutable arbitrary position, in which a 5- to 8-membered aromatic ring optionally containing 1 to 4 of an oxygen atom, a sulfur atom and/or a nitrogen atom in a ring is fused with one to four 5- to 8-membered aromatic carbocycle or other 5- to 8-membered aromatic heterocycle.

Examples of the "heteroaryl" include furyl (e.g. 2-furyl, 3-furyl), thienyl, (e.g. 2-thienyl, 3-thienyl), pyrrolyl (e.g. 1-pyrrolyl, 2-pyrrolyl, 3-pyrrolyl), imidazolyl (e.g. 1-imidazolyl, 2-imidazolyl, 4-imidazolyl), pyrazolyl (e.g. 1-pyrazolyl, 3-pyrazolyl, 4-pyrazolyl), triazolyl (e.g. 1,2,4-triazol-1-yl, 1,2,4-triazol-3-yl, 1,2,4-triazol-4-yl), tetrazolyl (e.g. 1-tetrazolyl, 2-tetrazolyl, 5-tetrazolyl), oxazolyl (e.g. 2-oxazolyl, 4-oxazolyl, 5-oxazolyl) , isoxazolyl (e.g. 3-isoxazolyl, 4-isoxazolyl, 5-isoxazolyl), thiazolyl (e.g. 2-thiazolyl, 4-thiazolyl, 5-thiazolyl), thiadiazolyl, isothiazolyl (e.g. 3-isothiazolyl, 4-isothiazolyl, 5-isothiazolyl), pyridyl (e.g. 2-pyridyl, 3-pyridyl, 4-pyridyl), pyridazinyl (e.g. 3-pyridazinyl, 4-pyridazinyl), pyrimidinyl (e.g. 2-pyrimidinyl, 4-pyrimidinyl, 5-pyrimidinyl), furazanyl (e.g. 3-furazanyl), pyrazinyl (e.g. 2-pyrazinyl), oxadiazolyl (e.g. 1,3,4-oxadiazol-2-yl), benzofuryl (e.g. 2-benzo[b]furyl, 3-benzo[b]furyl, 4-benzo[b]furyl, 5-benzo[b]furyl, 6-[benzo[b]furyl, 7-benzo[b]furyl], benzothienyl (e.g. 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g. 1-benzoimidazolyl, 2-benzoimidazolyl, 4-benzoimidazolyl, 5-benzoimidazolyl), dibenzofuryl, benzoxazolyl, quinoxalyl (e.g. 2-quinoxalinyl, 5-quinoxalinyl, 6-quinoxalinyl), cinnolinyl (e.g. 3-cinnolinyl, 4-cinnolinyl, 5-cinnolinyl, 6-cinnolinyl, 7-cinnolinyl, 8-cinnolinyl) , quinazolyl (e.g. 2-quinazolinyl, 4-quinazolinyl, 5-quinazolinyl, 6-quinazolinyl, 7-quinazolinyl, 8-quinazolinyl), quinolyl (e.g. 2-quinolyl, 3-quinolyl, 4-quinolyl, 5-quinolyl, 6-quinolyl, 7-quinolyl, 8-quinolyl), phthalazinyl (e.g. 1-phthalazinyl, 5-phthalazinyl, 6-phthalazinyl), isoquinolyl (e.g. 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g. 2-pteridinyl, 4-pteridinyl, 6-pteridinyl, 7-pteridinyl), carbazolyl, phenanthrydinyl, acridinyl (e.g. 1-acridinyl, 2-acridinyl, 3-acrydinyl, 4-acrydinyl, 9-acrydinyl), indolyl (e.g. 1-indolyl, 2-indolyl, 3-indolyl, 4-indolyl, 5-indolyl, 6-indolyl, 7-indolyl), isoindolyl, phanazinyl (e.g. 1-phenazinyl, 2-phenazinyl) and phenothiazinyl (e.g. 1-phenothiazinyl, 2-phenothiazinyl, 3-phenothiazinyl, 4-phenothiazinyl).

An alkyl part of the "alkoxy" has the same meaning as that of the "alkyl", and examples of the "alkoxy" include methoxy, ethoxy, n-propoxy, isopropoxy, n-butoxy, isobutoxy, and tert-butoxy.

The "alkoxycarbonyl" means carbonyl substituted with the "alkoxy", and examples include methoxycarbonyl, ethoxycarbonyl, n-propoxycarbonyl, isopropoxycarbonyl, n-butoxycarbonyl, isobutoxycarbonyl, tert-butoxycarbonyl and the like.

The "alkoxyalkyl" means the "alkyl" substituted with the "alkoxy", and examples include methoxymethyl, ethoxymethyl, n-propoxymethyl, isopropoxymethyl, n-butoxymethyl, isobutoxymethyl, tert-butoxymethyl, methoxyethyl, ethoxyethyl, n-propoxyethyl, isopropoxyethyl, n-butoxyethyl, isobutoxyethyl, and tert-butoxyethyl.

The "alkanoyl" means carbonyl substituted with the "alkyl" and examples include acetyl, propionyl, butyryl, isobutyryl, valeryl, isovaleryl, pivaloyl, hexanoyl, octanoyl, and lauroyl.

The "alkynyl" means alkynyl of a carbon number of 2 to 8 having one or more triple bonds in the "alkyl", and examples include ethynyl, 1-propynyl, 2-propynyl, 1-butynyl, 2-butynyl, 3-butynyl and the like.

The "alkylthio" means a group in which a sulfur atom is substituted with the "alkyl", and examples include methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, n-heptylthio, n-octylthio, n-nonylthio, n-decylthio and the like. Preferable is a group in which a sulfur atom is substituted with alkyl of a carbon number of 1 to 6.

The "haloalkyl" means the "alkyl" substituted with one or more halogens. Particularly, halogenated alkyl of a carbon number of 1 to 3 is preferable, and examples include trifluoromethyl, chloromethyl, dichloromethyl, 1,1-dichloroethyl, and 2,2,2-trichloroethyl.

The "haloalkoxy" means a group in which an oxygen atom is substituted with the "haloalkyl", and examples include trifluoromethoxy, chloromethoxy, dichloromethoxy, 1,1-dichloroethoxy, and 2,2,2-trichloroethoxy.

The "acyl" means carbonyl substituted with the "alkyl" and carbonyl substituted with the "aryl", and examples include acetyl, propionyl, butyryl, isobutyryl, valeryl, isovaleryl, pivaloyl, hexanoyl, octanoyl, lauroyl, benzoyl and the like.

When the "optionally substituted lower alkyl", the "optionally substituted lower alkenyl", the "optionally substituted lower alkoxy", the "optionally substituted cycloalkyl", the "optionally substituted cycloalkyl lower alkyl", the "optionally substituted lower alkylamino", the "optionally substituted heterocyclic group", the "optionally substituted aryl", the "optionally substituted aralkyl", the "optionally substituted lower alkanoyl", the "optionally substituted lower alkoxycarbonyl", the "optionally substituted heterocyclic carbonyl" the "optionally substituted cycloalkylcarbonyl", the "optionally substituted aryl carbonyl", the "optionally substituted nitrogen-containing aromatic heterocycle", the "optionally substituted heterocyclic lower alkyl", the "optionally substituted cycloalkyloxy", the "optionally substituted heterocyclic oxy", the "optionally substituted aryloxy", the "optionally substituted aralkyloxy" and the like have a substituent, they may be substituted with one to four same or different groups selected from a substituent group B at arbitrary positions.

Examples of a substituent group B include hydroxy, carboxy, halogen (F, Cl, Br, I), haloalkyl (e.g. $CF_3$, $CH_2CF_3$, $CH_2CCl_3$ etc.), alkyl (e.g. methyl, ethyl, isopropyl, tert-butyl etc.), alkenyl (e.g. vinyl), alkynyl (e.g. ethynyl), cycloalkyl (e.g. cyclopropyl), cycloalkenyl (e.g. cyclopropenyl), alkoxy (e.g. methoxy, ethoxy, propoxy, butoxy etc.), alkenyloxy (e.g. vinyloxy, aryloxy etc.), alkoxycarbonyl (e.g. methoxycarbonyl, ethoxycarbonyl, tert-butoxycarbonyl etc.), nitro, nitroso, optionally substituted amino (e.g. alkylamino (e.g. methylamino, ethylamino, dimethylamino etc.), acylamino (e.g. acetylamino, benzoylamino etc.), aralkylamino (e.g. benzylamino, tritylamino), hydroxyamino etc.), azide, aryl (e.g. phenyl etc.), aralkyl (e.g. benzyl etc.), cyano, isocyano, isocyanato, thiocyanato, isothiocyanato, mercapto, alkylthio (e.g. methylthio etc.), alkylsulfonyl (e.g. methanesulfonyl, ethanesulfonyl), optionally substituted carbamoyl (e.g. alkylcarbamoyl (e.g. methylcarbamoyl, ethylcarbamoyl, dimethylcarbamoyl etc.) etc.), sulfamoyl, acyl (e.g. formyl, acetyl etc.), formyloxy, haloformyl, oxalo, thioformyl, thiocarboxy, dithiocarboxy, thiocarbamoyl, sulfino, sulfo, sulfoamino, hydrazino, azido, ureido, amidino, guanidino, phthalimido, oxo and the like.

Examples of a substituent of the "optionally substituted amino" or the "optionally substituted carbamoyl" include optionally substituted alkyl (e.g. methyl, ethyl, isopropyl, benzyl carbamoylalkyl (e.g. carbamoylmethyl), mono or dialkylcarbamoylalkyl (e.g. dimethylcarbamoylethyl), hydroxyalkyl, heterocycloalkyl (e.g. morpholinoethyl, tetrahydropyranylethyl), alkoxycarbonylalkyl (e.g. ethoxycarbonylmethyl, ethoxycarbonylethyl), mono or dialkylaminoalkyl (e.g. dimethylaminoethyl) etc.),alkoxyalkyl (e.g. methoxyethyl, ethoxymethyl, ethoxyethyl, isopropoxyethyl etc.), acyl (e.g. formyl, optionally substituted alkylcarbonyl (e.g. acetyl, propionyl, butyryl, isobutyryl ,valelyl, isovaleryl, pivaloyl, hexanoyl, octanoyl, methoxyethylcarbonyl, 2,2,2-trifluoroethylcarbonyl, ethoxycarbonylmethylcarbonyl, alkoxyalkylcarbonyl (e.g. methoxyethylcarbonyl), alkylcarbamoylalkylcarbonyl (e.g. methylcarbamoylethylcarbonyl), alkoxycarbonylacetyl etc.), optionally substituted arylcarbonyl (e.g. benzoyl, toluoyl etc.), optionally substituted aralkyl (e.g. benzyl,. 4-fluorobenzyl etc.), hydroxy, optionally substituted alkylsulfonyl (e.g. methanesulfonyl, ethanesulfonyl, isopropylsulfonyl, 2,2,2-trifluoroethanesulfonyl, benzylsulfonyl, methoxyethylsulfonyl, etc.), arylsulfonyl optionally substituted with alkyl or halogen (e.g. benzenesulfonyl, toluenesulfonyl, 4-fluorobenzenesulfonyl), cycloalkyl,(e.g. cyclopropyl etc.), aryl optionally substituted with alkyl (e.g. phenyl, trityl etc.), alkylaminosulfonyl (e.g. methylaminosulfonyl, dimethylaminosulfonyl etc.), alkylaminocarbonyl (e.g. dimethylaminocarbonyl etc.), alkoxycarbonyl (e.g. ethoxycarbonyl etc.), cycloalkylcarbonyl (e.g. cyclopropylcarbonyl, cyclohexylcarbonyl etc.), optionally substituted sulfamoyl (e.g. sulfamoyl, methylsulfamoyl, dimethylsulfamoyl etc.), alkylcarbonylamino (e.g. methylcarbonylamino), heterocycle (e.g. morpholino, tetrahydropyranyl), optionally substituted amino (e.g. mono or dialkylamino (e.g. dimethylamino), formylamino) and the like. Preferable is methyl. The substituent may be mono- or di-substituted.

The amino group of the "optionally substituted amino", the "optionally substituted carbamoyl" or the "optionally substituted carbamoyl carbonyl" may be such that two substituents of an amino group together with an adjacent nitrogen atom form a nitrogen-containing heterocycle (preferably 5- to 7-membered ring, preferably saturated) optionally containing a sulfur atom and/or an oxygen atom in a ring, and the ring may be substituted with oxo or hydroxy. A sulfur atom forming a ring may be substituted with oxo. A 5-membered or 6-membered ring such as piperazinyl, piperidino, morpholino, pyrrolidino, thiadinan-2-yl, 2-oxopiperidino, 2-oxopyrrolidino, 1,1-dioxide-1,2-thiazinan-2-yl, 4-hydroxymorpholino and the like is preferable.

(More preferable aspect)

Y may be a divalent group, and examples include optionally substituted imino, O, S, SO and $SO_2$. Preferably, Y is optionally substituted imino, specifically, a group represented by —$N(R^4)$— (wherein $R^4$ is hydrogen, optionally substituted lower alkyl, optionally substituted aryl or optionally substituted aralkyl), or —O—. Preferable examples of a substituent of optionally substituted lower alkyl or optionally substituted aryl of $R^4$ include halogen, lower alkoxy, amino, and hydroxy. $R^4$ is preferably hydrogen, lower alkyl, phenyl or benzyl.

In $R^4$, an acyl group represented by the 1), or a N atom in a C ring represented by the 2) is particularly important from a viewpoint of the pharmacological activity, and other partial structure can take various structures as far as the main pharmacological activity is not adversely influenced.

$R^4$ is 1) a group represented by the formula: —$COR^5$ (wherein $R^5$ is a group selected from a substituent group A).

The substituent group A includes hydrogen, hydroxy, optionally substituted lower alkyl, optionally substituted lower alkoxy, optionally substituted cycloalkyl, optionally substituted cycloalkyloxy, optionally substituted amino, optionally substituted aminooxy, optionally substituted heterocyclic group, optionally substituted heterocyclic oxy, optionally substituted aryl, optionally substituted aryloxy, optionally substituted aralkyl, optionally substituted aralkyloxy, formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, and optionally substituted arylcarbonyl.

Preferable examples of a substituent of the optionally substituted lower alkyl, the optionally substituted lower alkoxy, or the optionally substituted cycloalkyl include hydroxy, halogen, amino, and lower alkoxy (e.g. methoxy, ethoxy). Preferable examples of a substituent of the optionally substituted amino include lower alkyl (e.g. methyl, ethyl, dimethyl), lower alkoxy (e.g. methoxy, ethoxy), optionally substituted aryl, and optionally substituted aralkyl (e.g. benzyl, 4-F-benzyl). Preferable examples of a substituent of the optionally substituted heterocyclic group, or the optionally substituted aryl include lower alkyl, lower alkoxy, amino, lower alkylamino, di-lower alkylamino, hydroxy, and halogen.

$R^5$ is preferably hydrogen, hydroxy, optionally substituted lower alkyl (example of substituent: hydroxy, lower alkoxy), optionally substituted lower alkoxy (example of substituent: hydroxy, lower alkoxy), optionally substituted amino (example of substituent: lower alkyl, hydroxy lower alkyl, lower alkoxy, lower alkoxy lower alkyl, phenyl, benzyl, 4-fluorobenzyl), phenyl, optionally substituted phenoxy (e.g. phenoxy, 4-fluorophenyloxy), optionally substituted benzyl (e.g. benzyl, 4-fluorobenzyl), optionally substituted benzyloxy (e.g. benzyloxy, 4-fluorobenzyloxy), morpholino, morpholinooxy, 2,2-dimethylhydrazino, methoxyamino and the like. In another aspect, preferable examples of $R^5$ include formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, and optionally substituted arylcarbonyl. Preferable examples of a substituent of the "optionally substituted" of them include lower alkyl, lower alkoxy, amino, lower alkylamino, hydroxy, halogen, and phenyl.

When $R^5$ is heterocyclic carbonyl, as the heterocycle, the C ring is exemplified, and $R^4$ can take a structure shown below. In this case, a position of a nitrogen atom in the C ring may be a position other than a part adjacent to a bond, and is not limited to the following structure.

[Chemical formula 6]

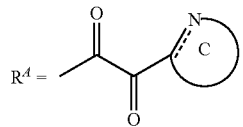

In another aspect of the present invention, $R^4$ is 2) a group represented by the formula:

[Chemical formula 7]

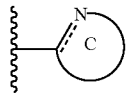

(wherein a C ring is an optionally substituted nitrogen-containing aromatic heterocycle in which, among atoms adjacent to an atom having a bond, at least one atom is an unsaturated nitrogen atom, and a broken line represents the presence or the absence of a bond).

The C ring means a nitrogen-containing aromatic heterocycle in which, among atoms adjacent to a binding site, at least one atom is an unsaturated nitrogen atom. A broken line indicates the presence or the absence of a bond. A curve part means atoms and bonds constituting a C ring, and those atoms and bonds may be selected so that a C ring exhibits the aromatic property. A C ring is preferably such that atoms at a binding site are a carbon atom, the carbon atom is bound with one atom of adjacent atoms via a double bond, and is bound with other atom of adjacent atoms via a single bond.

A C ring is preferably a 5- to 8-membered ring, more preferably a 5- or 6-membered ring, and may be a fused ring with other ring (e.g. carbocycle, heterocycle). The C ring may contain, in addition to one N atom, further, 1 to 4, preferably 1 to 3 same or different hetero atoms selected from the group consisting of O, S and N atoms. The C ring preferably contains 1 to 3 N atoms, or contains 1 or 2 N atoms, and contains one O or S atom. Specific examples are shown below.

[Chemical formula 8]

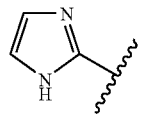

(C-1)

-continued
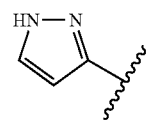 (C-2)
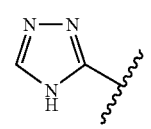 (C-3)
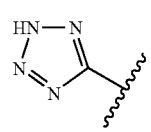 (C-4)
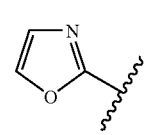 (C-5)
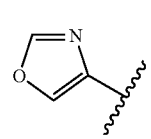 (C-6)
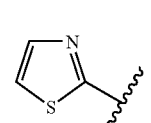 (C-7)
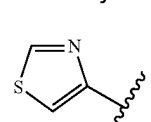 (C-8)
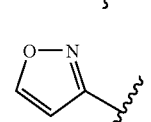 (C-9)
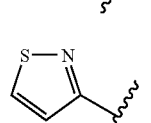 (C-10)
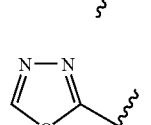 (C-11)
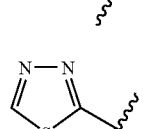 (C-12)
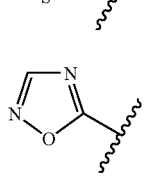 (C-13)
-continued
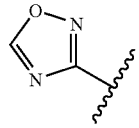 (C-14)
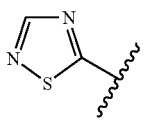 (C-15)
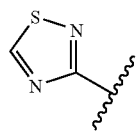 (C-16)
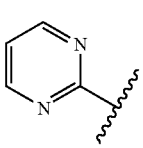 (C-17)
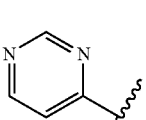 (C-18)
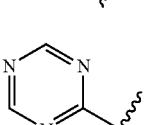 (C-19)
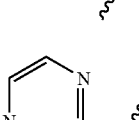 (C-20)
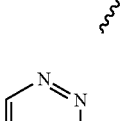 (C-21)
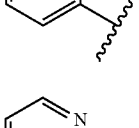 (C-22)
The C ring is more preferably a ring shown below.
[Chemical formula 9]
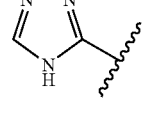 (C-3)

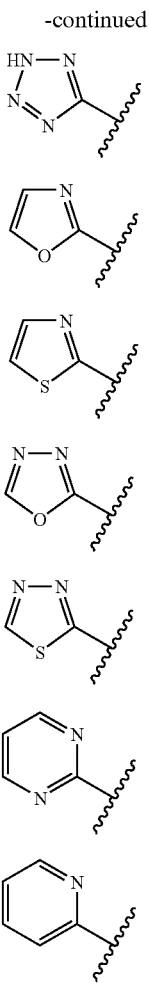

An example in which the C ring is a fused ring means heteroaryl in which one to four 5- to 8-membered aromatic carbocycles (5-to 8-membered aromatic carbocycles) and/or other 5- to 8-membered aromatic heterocycles (5- to 8-membered aromatic heterocycles optionally containing one to four of an O atom, a S atom, and/or a N atom in a ring). Examples include benzimidazol-2-yl, benzoxazol-2-yl, quinoxalin-2-yl, cinnolin-3-yl, quinazolin-2-yl, quinazolin-4-yl, quinolin-2-yl, phthalazin-1-yl, isoquinolin-1-yl, isoquinolin-3-yl, purin-2-yl, purin-6-yl, purin-8-yl, pteridin-2-yl, pteridin-4-yl, pteridin-6-yl, pteridin-7-yl, carbazol-1-yl, phenanthridine-6-yl, indol-2-yl, isoindol-1-yl and the like.

When the C ring is substituted, more preferable examples of a substituent include hydrogen, optionally substituted lower alkyl (example of substituent: hydroxy, lower alkoxy, amino, halogen), optionally substituted aryl (e. g. phenyl, 4-fluorophenyl), optionally substituted aralkyl (e.g. benzyl, 4-fluorobenzyl), optionally substituted aryloxy (e.g. phenyloxy, 4-fluorophenyloxy), optionally substituted aralkyloxy (e.g. benzyloxy, 4-fluorobenzyloxy), heterocyclic group (e.g. morpholino), optionally substituted amino (example of substituent: lower alkyl (e.g. methyl, ethyl), amino, mono- or di-lower alkylamino., lower alkoxy (e.g. methoxy, ethoxy)), halogen, hydroxy, lower alkylcarbonyl (e.g. acetyl), lower alkoxycarbonyl (e.g. methoxycarbonyl), and optionally substituted carbamoyl (example of substituent: lower alkyl). Further preferable examples include $R^{7a}$ and $R^{7b}$ described later, that is, (1) hydrogen, (2) methyl, (3) ethyl, (4) n-propyl, (5) isopropyl, (6) 2-hydroxyethyl, (7) 2-methoxyethyl, (8) phenyl, (9) benzyl, (10) morpholine, (11) 1,1-dimethylhydradine, (12) O-methylhydroxylamine, (13) halogen, (F, Cl, Br, I), (14) hydroxy, (15) acetyl, (16) methoxycarbonyl, (17) carbamoyl, (18) 4-fluorobenzyl, (19) 4-fluorophenyloxy, (20) 4-fluorobenzyloxy and the like. These substituents may be the same or different, and can replace at 1 to 3, preferably 1 to 2 positions on the C ring.

The C ring is more preferably a group represented by $R^4$-4 to $R^4$-11 described in Examples described later.

$R^1$ is hydrogen or lower alkyl, preferably hydrogen or lower alkyl of a carbon number of 1 to 3 (e.g. methyl), and particularly preferably hydrogen.

X is a single bond, a hetero atom group (hereinafter, referred to as M in some cases) selected from O, S, SO, $SO_2$ and NH, or lower alkylene or lower alkenylene in which the hetero atom group may intervene. Herein, the "intervene" means the case 1) in which the hetero atom group is present between carbon atoms constituting alkylene or alkenylene, the case 2) in which the hetero atom group is bound to a N atom of a carbamoyl group adjacent to X, and/or the case 3) in which the hetero atom group is bound to $R^2$ adjacent to X. In addition, the hetero atom group (M) may be one or more-same or different groups. For example, as the case in which the hetero atom group intervenes in lower alkylene, there can be exemplified —M—$CH_2$—, —$CH_2$—M—$CH_2$—, —$CH_2$—M—, and —$CH_2$—M—M—$CH_2$—. X is preferably a spacer in which one to three atoms are bound. X is more preferably lower alkylene or lower alkenylene in which a hetero atom group may intervene, or O, further preferably lower alkylene of a carbon number of 1 to 3 or lower alkenylene of a carbon number of 2 to 3, or O, particularly preferably methylene or O.

$R^2$ is a group selected from the substituent group A, preferably optionally substituted aryl. The aryl is preferably phenyl. As a substituent on the aryl, there can be preferably exemplified 1 to 3, preferably 1 to 2 same or different substituents selected from the group consisting of halogen, hydroxy, amino, lower alkylamino, cyano, carboxy, formyl, oxo, lower alkyl, lower alkoxy, lower alkylthio, carbamoyl, and lower alkylcarbamoyl, more preferably, the substituent is selected from halogen, hydroxy, amino, cyano, lower alkyl, and lower alkoxy, and the substituent is particularly preferably halogen (e.g. F). A position of the substituent on aryl is preferably a 4-position. $R^2$ is more preferably phenyl optionally substituted with halogen, further preferably phenyl, or phenyl substituted with at least halogen. Particularly preferably is 4-halogen phenyl (e.g. 4-F-phenyl).

$R^3$ may be various substituents as far as they do not adversely influence on the pharmacological activity of Compound (I), and examples include hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl. Examples of a substituent of the "optionally substituted" include halogen, hydroxy, amino, lower alkyl amino, cyano, carboxy, formyl, oxo, lower alkyl, lower alkoxy, lower alkylthio, carbamoyl, lower alkylcarbamoyl, aryl, heterocyclic group, lower alkylcarbonyl, lower alkylcarbonyloxy, lower alkoxycarbonyl, halogenated lower alkyl, and halogenated lower alkoxy. $R^3$ is preferably hydrogen or lower alkyl (e.g. methyl), more preferably hydrogen.

Compound (I) more preferably includes the following aspects.

(1) The case in which Y is $NR^4$ (wherein $R^4$ is hydrogen, optionally substituted lower alkyl (e.g. methyl), optionally substituted aryl (e.g. phenyl), optionally substituted aralkyl (e.g. benzyl)) or O, preferably $NR^4$ (wherein $R^4$ is hydrogen, lower alkyl (e.g. methyl), phenyl or benzyl) or O, more preferably NH; $R^A$ is a group represented by the formula: —$COR^5$ ($R^5$ is a group selected from a substituent group A); $R^1$ is hydrogen or lower alkyl (e.g. methyl), preferably hydrogen, X is a single bond, a hetero atom group selected from O, S, SO, $SO_2$ and NH, or lower alkylene or lower alkenylene in which the hetero atom group may intervene, preferably lower alkylene or lower alkenylene in which the heteroatom group may intervene, or O, more preferably $C_1$-$C_3$ alkylene or $C_2$-$C_3$ alkenylene in which the hetero atom group may intervene, or O, particularly preferably methylene; $R^2$ is optionally substituted aryl, preferably optionally substituted phenyl, more preferably phenyl optionally substituted with halogen.

In this case, $R^5$ is preferably lower alkoxy (e.g. methoxy, ethoxy), amino, mono- or di-lower alkylamino (e.g. methylamino, dimethylamino), or hydroxy, more preferably lower alkoxy. In another aspect, $R^5$ is preferably formyl, carboxy, optionally substituted lower alkanoyl, optionally substituted lower alkoxycarbonyl, optionally substituted carbamoyl, optionally substituted heterocyclic carbonyl (e.g. the C ring), optionally substituted cycloalkylcarbonyl, or optionally substituted arylcarbonyl.

$R^3$ is preferably hydrogen, halogen, hydroxy, or lower alkyl, more preferably hydrogen.

(2) The case where Y is $NR^4$ (wherein $R^4$ is hydrogen, optionally substituted lower alkyl (e.g. methyl), optionally substituted aryl (e.g. phenyl)), optionally-substituted aralkyl (e.g. benzyl)), or O, preferably $NR^4$ (wherein $R^4$ is hydrogen, lower alkyl (e.g. methyl), phenyl or benzyl), or O, more preferably NH; $R^A$ is a nitrogen-containing aromatic heterocyclic group (C ring) represented by the 2) ; $R^1$ is hydrogen or lower alkyl (e.g. methyl), preferably hydrogen, X is a single bond, a hetero atom group selected from O, S, SO, $SO_2$ and NH, or lower alkylene or lower alkyeylene in which the hetero atom group may intervene, preferably lower alkylene or lower alkenylene in which the hetero atom group may intervene, or O, more preferably $C_1$-$C_3$ alkylene or $C_2$-$C_3$ alkenylene in which the hetero atom group may intervene, or O, particularly preferably methylene; $R^2$ is optionally substituted aryl, preferably optionally substituted phenyl, more preferably phenyl optionally substituted with halogen.

In this case, $R^3$ is preferably hydrogen, halogen, hydroxy, lower alkyl, more preferably hydrogen.

(3) The case where Y is O, S, SO or $SO_2$, preferably O; $R^A$ is a group represented by the formula: —$COR^5$ (wherein $R^5$ is a group selected from a substituent group A); $R^1$ is hydrogen, or lower alkyl (e.g. methyl), preferably hydrogen, X is a single bond, a hetero atom group selected from O, S, SO, $SO_2$ and NH, or lower alkylene or lower alkenylene in which the hetero atom group may intervene, preferably lower alkylene, or lower alkenylene in which the hetero atom group may intervene, or O, more preferably $C_1$-$C_3$ alkylene or $C_2$-$C_3$ alkenylene in which the hetero atom group may intervene, or O, particularly preferably methylene; $R^2$ is optionally substituted aryl, preferably optionally substituted phenyl, more preferably phenyl optionally substituted with halogen.

In this case, $R^5$ is preferably lower alkoxy (e.g. methoxy, ethoxy), amino, mono- or di-lower alkylamino (e.g. methylamino, dimethylamino), or hydroxy, more preferably lower alkoxy. $R^3$ is preferably hydrogen, halogen, hydroxy, or lower alkyl, more preferably hydrogen. In addition, in another aspect, $R^5$ is preferably formyl, carboxy, optionally substituted lower alkanoyl, optionally substituted lower alkoxycarbonyl, optionally substituted carbamoyl, optionally substituted heterocyclic carbonyl (e.g. the C ring), optionally substituted cycloalkylcarbonyl, or optionally substituted arylcarbonyl.

(4) The case where Y is O, S, SO or $SO_2$, preferably O; $R_A$ is a nitrogen-containing aromatic heterocyclic group (C ring) represented by the 2); $R^1$ is hydrogen or lower alkyl, preferably hydrogen, X is a single bond, a hetero atom group selected from O, S, SO, $SO_2$ and NH, or lower alkylene, or lower alkenylene in which the hetero atom group may intervene, preferably lower alkylene or lower alkenylene in which the hetero atom group may intervene, or O, more preferably $C_1$-$C_3$ alkylene or $C_2$-$C_3$ alkenylene in which the hetero atom group may intervene, or O, particularly preferably methylene; $R_2$ is optionally substituted aryl, preferably optionally substituted phenyl, more preferably phenyl optionally substituted with halogen.

In this case, $R^3$ is preferably hydrogen, halogen, hydroxy, or lower alkyl, more preferably hydrogen.

(5) The case where Y is $NR^4$ (wherein $R^4$ is hydrogen, optionally substituted lower alkyl (e.g. methyl), optionally substituted aryl (e.g. phenyl)), optionally substituted aralkyl (e.g. benzyl)), O or S; $R^A$ is a nitrogen-containing aromatic heterocyclic group represented by the 2) (C ring, preferably, C-3, C-5, C-7, C-11, C-12, C-17, or C-22, more preferably $R^A$-4, $R^A$-5, $R^A$-6, $R^A$-7, $R^A$-8, $R^A$-10, or $R^A$-11, each may be substituted); $R^1$ is hydrogen or lower alkyl, preferably hydrogen, $R^2$-X is hydrogen, lower alkyl, optionally substituted lower alkyl (example of substituent: hydroxy, lower alkoxy), phenyl, aralkyl (e.g. benzyl), heterocyclic group (preferably 5- to 7- membered ring), 1,1-dimethylhydrazine, or O-methylhydroxylamine.

In this case, $R^3$ is preferably hydrogen, halogen, hydroxy, or lower alkyl, more preferably hydrogen.

(6) The case where Y is $NR^4$ (wherein $R^4$ is hydrogen, optionally substituted lower alkyl (e.g. methyl), optionally substituted aryl (e.g. phenyl,)), optionally substituted aralkyl (e.g. benzyl)), O or S; $R^A$ is —$COR^5$ (wherein $R^5$ is optionally substituted amino (example of substituent: aralkyl (e.g. benzyl), substituted aralkyl. (e.g. 4-F-benzyl)), optionally substituted aralkyloxy (e.g. benzyloxy, 4-F-benzyloxy)); $R^1$ is hydrogen or lower alkyl, preferably hydrogen, $R^2$-X is hydrogen, lower alkyl, substituted lower alkyl (example of substituent: hydroxy, lower alkoxy), phenyl, aralkyl (e.g. benzyl), heterocyclic group (preferably 5- to 7-membered ring), 1,1-dimethylhydrazine, or O-methylhydroxyamine.

In this case, $R^3$ is preferably hydrogen, halogen, hydroxy, or lower alkyl, or more preferably hydrogen.

Compound (I) has at least the following characteristics as its chemical structure.

(1) Oxo (═O), hydroxy (OH) and $R^A$ are adjacently bound on a heterocycle which is a main skeleton, and $R^A$ has a hetero atom (O or N) at a site adjacent to a carbon atom bound to the heterocycle.

(2) A site adjacent to oxo on a heterocycle which is a main skeleton has a substituted carbamoyl group (—$CONR^1XR^2$). $R^2$ a group selected from the substituent group A, preferably optionally substituted aryl.

By having such the structure, the very strong integrase inhibitory activity and/or cell proliferation inhibitory activity are exhibited against a virus including HIV.

The present invention also provides a pharmaceutically acceptable salt of Compound (I) and a solvate thereof. Theoretically possible all tautomers, geometrical isomers and the like of the present compound are within the scope of the present invention.

Examples of the pharmaceutical acceptable salt of the present compound include, as a basic salt, alkali metal salts such as sodium salt, potassium salt etc.; alkaline earth metal salts such as calcium salt, magnesium salt etc.; ammonium salts; aliphatic amine salts such as trimethylamine salt, triethylamine salt, dicyclohexylamine salt, ethanolamine salt, diethanolamine salt, triethanolamine salt, brocaine salt, meglumine salt, diethanolamine salt and ethylenediamine salt; aralkylamine salt such as N,N-dibenzylethylenediamine salt, benethamine salt etc.; heterocyclic aromatic amine salts such as pyridine salt, picoline salt, quinoline salt, isoquinoline salt etc.; quaternary ammonium salts such as tetramethylammonium salt, tetraethylammonium salt, benzyltrimethylammonium salt, benzyltriethylammonium salt, benzyltributylammonium salt, methyltrioctylammonium salt, tetrabutylammonium-salt and the like; basic amino acid salts such as alginine salt, lysine salt etc. Examples of an acidic salt include inorganic acid salts such as hydrochloride, sulfate, nitrate, phosphate, carbonate, hydrogencarbonate, perchlorate etc.; organic acid salts such as acetate, propionate, lactate, maleate, fumarate, taltrate, malate, citrate, ascorbate etc.; sulfonates such as methanesulfonate, isethionate, benzenesulfonate, p-toluenesulfonate etc.; acidic amino acids such as aspartate, glutamate etc.

Examples of a solvate of the present compound include alcoholate, hydrate and the like.

A general process for producing the present compound will be exemplified below.

(Process 1)

The case where Y=NH, RA=—$COR^5$ (Compounds I-A, I-B, I-C)

[Chemical formula 10]

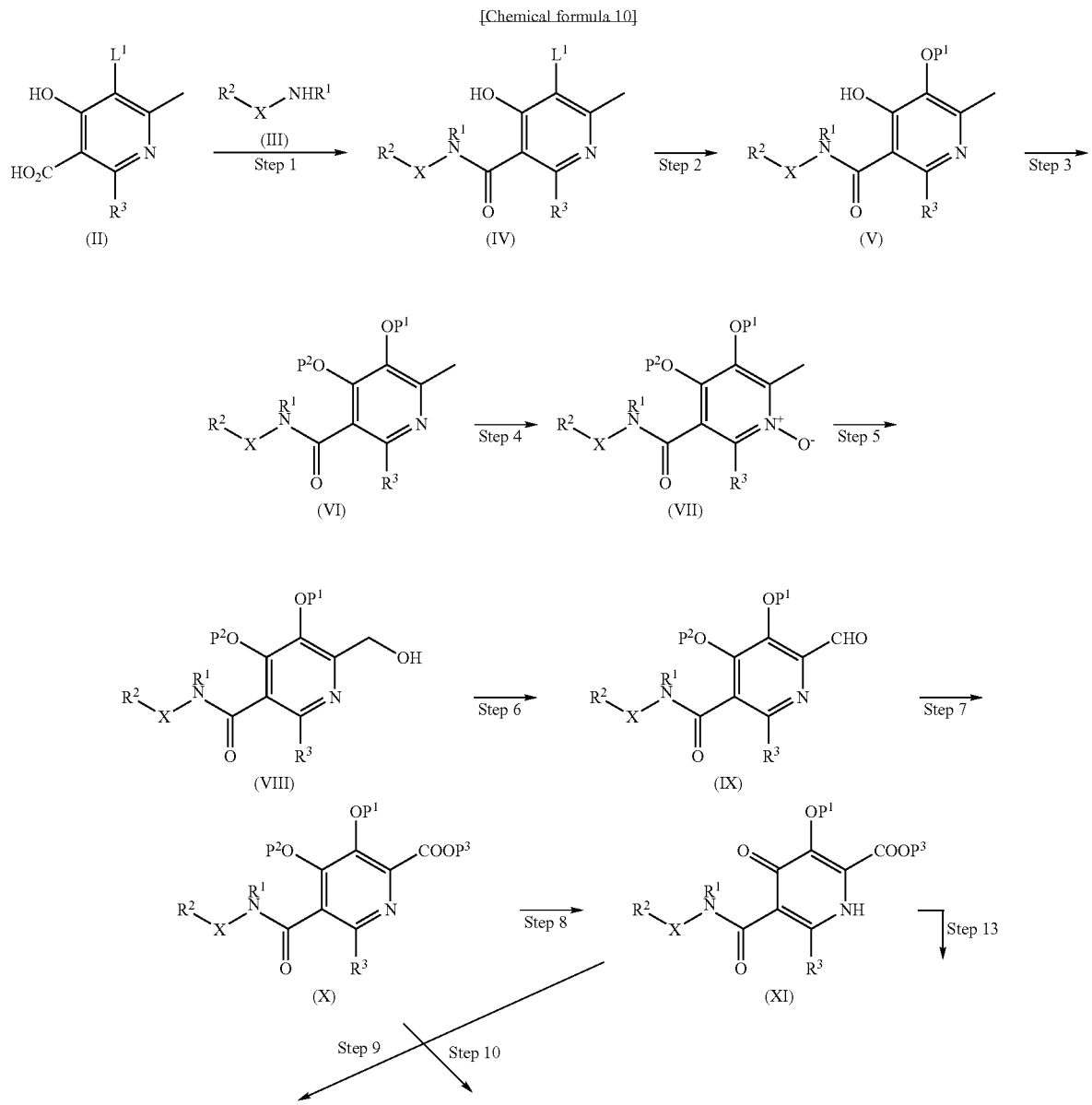

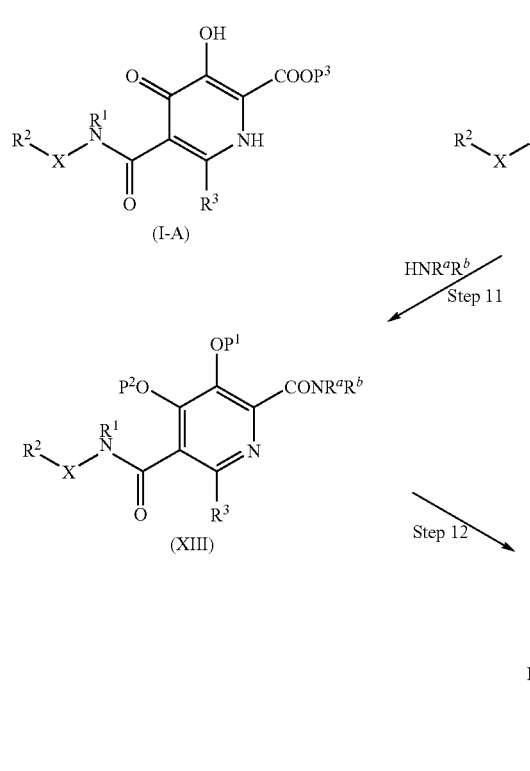

(wherein $L^1$ is a leaving group (e.g. halogen); $P^1$ and $P^2$ are a hydroxy protecting group; $P^3$ is a carboxy protecting group (e.g. lower alkyl); $R^a$ and $R^b$ are hydrogen or a substituent on an amino group)

Examples of the hydroxy protecting group ($P^1$, $P^2$) include acyl (e.g. acetyl, pivaloyl, benzoyl), aralkyl (e.g. benzyl), lower alkyl (e.g. methyl), alkoxy alkyl (e.g. methoxymethyl, methoxyethyl), lower alkylsulfonyl (e.g. methanesulfonyl), arylsulfonyl (e.g. benzenesulfonyl, toluenesulfonyl), alkoxycarbonyl (e.g. methoxycarbonyl) and the like.

Examples of the carboxy protecting group ($P^3$) include lower alkyl (e.g. methyl, ethyl), and aralkyl (e.g. benzyl).

(First Step)

The present step is a reaction for condensing Compound (II) and Compound (III) to produce Compound (IV). The reaction may be performed according to the condition for a reaction of amidating carboxylic acid which is generally performed. Compound (II) may be reacted as it is, or may be reacted after it is converted into corresponding acid chloride or active ester. Preferably, the reaction is performed in a suitable solvent in the presence of a condensing agent.

As the condensing agent, dicyclohexylcarbodiimide, 1-ethyl-3-(3-dimethylaminopropyl) carbodiimide hydrochloride and the like can be used. If necessary, a reagent such as 1-hydroxybenzotriazole, N-hydroxysuccineimide and the like, and a base such as triethylamine, N-methylmorpholine, and pyridine may be added.

A reaction temperature is 0 to 150° C., preferably room temperature to 70° C.

As a reaction solvent, an aprotic solvent can be widely used, and tetrahydrofuran (THF), 1,4-dioxane, dimethylformamide (DMF), methylene chloride, chloroform and the like are preferable.

A reaction time is a few minutes to a few tens hours, preferably 9 to 17 hours.

(Second Step)

The present step is a reaction for introducing a protecting hydroxy group ($OP^1$) into Compound (IV) to produce Compound (V). The reaction may be performed according to condition for an alkoxylating reaction which is generally performed.

For example, by reacting metal alkoxide (e.g. MeONa) with Compound (IV), Compound (V) in which $P^1$ is methyl can be synthesized.

A reaction temperature is 0 to 200° C., preferably 80 to 200° C.

Examples of a reaction solvent include alcohol, dimethylformamide (DMF), and dimethyl sulfoxide (DMSO).

A reaction time is a few minutes to a few tens hours, preferably 2 to 4 hours.

(Third Step)

The present step is a reaction for protecting hydroxy of Compound (V) to produce Compound (VI). The reaction may be performed according to condition for a reaction of protecting hydroxy which is generally performed. For example, by using diisopropyl azodicarboxylate or diethyl azodicarboxylate together with alcohol and various phosphines, Compound (VI) in which $P^2$ is alkyl can be synthesized.

A reaction temperature is 0 to 100° C., preferably 0° C. to room temperature.

Examples of a reaction solvent include THF, toluene, dichloromethane and the like.

A reaction time is a few minutes to a few tens hours, preferably 1 to 3 hours.

(Fourth Step)

The present step is a reaction of oxidizing a N atom of Compound (VI) to produce Compound (VII). The reaction may be performed according to .condition for an oxidation reaction using an oxidizing agent which is generally performed.

A reaction temperature is O to 100° C., preferably from under ice-cooling to room temperature.

Examples of a reaction solvent include chloroform, methylene chloride, acetic acid and the like.

Examples of the oxidizing agent include metachloroperbenzoic acid, hydrogen peroxide and the like.

A reaction time is a few minutes to a few tens hours, preferably 1 to 5.

(Fifth Step)

The present step is a reaction for hydroxylating a methyl group of Compound (VII). Preferably, after the methyl group is reacted with acetic anhydride to acetoxylate it (reaction temperature: 0 to 150° C., preferably room temperature to 100° C.), this may be hydrolyzed,(e.g. treatment with a base (e.g. alkali hydroxide metal)).

A reaction time is a few minutes to a few tens hours, preferably 0.5 to 2 hours for acetoxylation, and 0.5 to 1 hour for hydrolysis.

(Sixth Step)

The present step is a reaction for oxidizing hydroxy of Compound (VIII) to synthesize Compound (IX).

A reaction temperature is 0 to 150° C., preferably room temperature to 70° C.

Examples of a reaction solvent include chloroform and the like.

Examples of an oxidizing agent include dimethyl sulfoxide and the like.

A reaction time is a few minutes to a few tens hours, preferably 0.1 to 1 hour.

(Seventh Step)

The present step is a reaction for oxidizing formyl of Compound (IX) to synthesize Compound (X).

A reaction temperature is 0 to 150° C., preferably from under ice-cooling to room temperature.

Examples of a reaction solvent include alcohol and the like.

Examples of the oxidizing agent include potassium hydroxide and iodine.

A reaction time is a few minutes to a few tens hours, preferably 0.5 to 3 hours.

(Eighth Step)

The present step is a reaction for deprotecting an $OP^2$ part of Compound (X) to synthesize Compound,(XI). The reaction may be performed according to the condition for a reaction of deprotecting a hydroxy protecting group which is generally performed.

A reaction temperature is 0 to 150° C., preferably from under ice-cooling to room temperature.

Examples of a reaction solvent include acetonitrile, methylene chloride, tetrahydrofuran (THF) and the like.

A reaction time is a few minutes to a few tens hours, preferably 1 to 3 hours.

(Ninth Step)

The present step is a reaction for deprotecting an $OP^1$ part of Compound (XI) to synthesize the present compound (I-A). The reaction may be performed by treatment with preferably a Lewis acid (e.g. aluminum chloride).

A reaction temperature is 0 to 150° C., preferably 10 to 50° C.

Examples of a reaction solvent include methylene chloride, THF and the like.

A reaction time is a few minutes to a few tens hours, preferably 1 to 3 hours.

(Tenth Step)

The present step is a reaction for deprotecting an ester part ($COOP^3$ of Compound (X) to synthesize carboxylic acid (XII). Preferably, the ester part maybe hydrolyzed with an alkali (e.g. NaOH).

A reaction temperature is 0 to 150° C., preferably 10 to 50° C.

Examples of the reaction solvent include methanol, water and the like.

A reaction time is a few minutes to a few tens hours, preferably a few minutes to 2 hours.

Carboxylic acid (XII) may be converted into various derivatives (e.g. amide).

(Eleventh Step)

The present step is a reaction for reacting various amines with Compound (XII) to synthesize Compound (XIII). The reaction may be performed according to the condition for a reaction of amidating carboxylic acid which is generally performed; for example, the reaction may be performed as in the first step.

A reaction temperature is 0 to 150° C., preferably room temperature to 70° C.

As a reaction solvent, an aprotic solvent can be widely used, and tetrahydrofuran (THF), 1,4-dioxane, dimethylformamide (DMF), methylene chloride, chloroform and the like are preferable.

A reaction time is a few minutes to a few tens hours, preferably a few minutes to 3 hours.

An amide part of the resulting Compound (XIII) may be further chemically modified (e.g. N-alkylated).

(Twelfth Step)

The present step is a reaction for deprotecting $OP^1$ and $OP^2$ parts of Compound (XIII) to synthesize the present compound (I-B). The reaction may be performed according to the condition for a reaction of deprotecting a hydroxy protecting group which is generally performed.

For example, when pyridine hydrochloride is used, a reaction temperature is 0 to 200° C., preferably 150 to 180 degree.

A reaction time is a few minutes to a few tens hours, preferably 1 to 5 minutes.

(Thirteenth Step)

The present step is a reaction for deprotecting an ester part ($COOP^3$) of Compound (XI) to synthesize carboxylic acid (XIV). Preferably, the ester part may be hydrolyzed with an alkali (e.g. LiOH).

A reaction temperature is 0 to 150° C., preferably 10 to 50° C.

Examples of a reaction solvent include methanol, water and the like.

A reaction time is a few minutes to a few tens hours, preferably a few minutes to 3 hours.

(Fourteenth Step)

The present step is a reaction for deprotecting an $OP^1$ part of Compound (XIV) to synthesize the present compound (I-C). The reaction may be performed by treatment with preferably a Lewis acid (e.g. boron tribromide).

A reaction temperature is 0 to 150° C., preferably from under ice-cooling to room temperature.

Examples of a reaction solvent include dichloromethane and the like.

A reaction time is a few minutes to a few tens hours, preferably a few minutes to 5 hours.

(Process 2)

The case of heterocyclic group in which Y=NH, and $R^4$=C ring (Compound I-D)

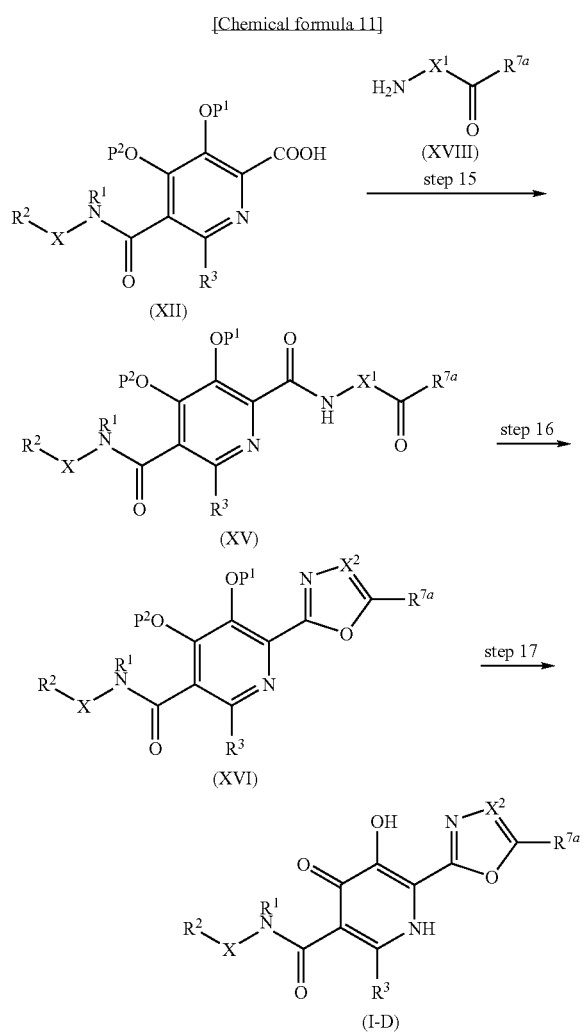

(wherein $X^1$ is NH or $CHR7^b$; $X^2$ is N or $CR7^b$; $7^a$ and $7^b$ are a substituent on a heterocycle; other symbols are as defined above)

(Fifteenth Step)

The present step is a reaction for condensing Compound (XII) and Compound (XVIII) to produce Compound (XV). The reaction may be performed according to the condition for a reaction of amidating carboxylic acid which is generally performed. Compound (XII) may be reacted as it is, or may be reacted after it is converted into corresponding acid chloride or active ester. Preferably, the reaction is performed in a suitable solvent in the presence of a condensing agent.

As the condensing agent, dicyclohexylcarbodiimide, 1-ethyl-3-(3-dimethylaminopropyl)carbodiimide hydrochloride and the like can be used. If necessary, a reagent such as 1-hydroxybenzotriazole, N-hydroxysuccinimide and the like, and a base such as triethylamine, N-methylmorpholine, and pyridine may be added.

A reaction temperature is 0 to 150° C., preferably room temperature to 70° C.

As a reaction solvent, an aprotic solvent can be widely used, and tetrahydrofuran (THF), 1,4-dioxane, dimethylformaide (DMF), methylene chloride, chloroform and the like are preferable.

A reaction time is a few minutes to a few tens hours, preferably 9 to 17 hours.

(Sixteenth Step)

The present step is a reaction for performing a dehydration and cyclization reaction to produce Compound (XVI) from Compound (XV). The reaction may be performed according to the condition for a dehydration reaction which is generally performed. For example, by reacting phosphorus oxychloride with Compound (XV), Compound (XVI) can be synthesized.

A reaction temperature is 0 to 150° C., preferably room temperature to 100° C.

As a reaction solvent, toluene, methylene chloride, chloroform and the like are preferable.

A reaction time is a few minutes to a few tens hours, preferably 1 to 3 hours.

(Seventeenth Step)

The present step is a reaction for deprotecting $OP^1$ and $OP^2$ parts of Compound (XVI) to synthesize the compound (I-D). The present step may be performed according to the twelfth step.

Alternatively, the present compound obtained above may be chemically modified to synthesize another compound. In the reaction, when a reactive functional group (e.g. OH, COOH, $NH_2$) is present in a side chain part, if desired, the group may be protected before a reaction, and deprotected after a reaction.

The present invention further provides Compounds (I'), (I''') or (I''') as an intermediate for synthesizing Compound (I). By deprotecting these compounds according to the condition for a deprotection reaction in the Process 1 or 2, Compound (I) is obtained.

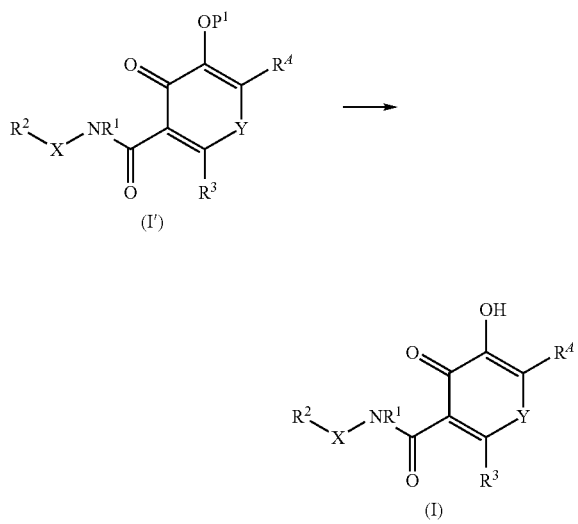

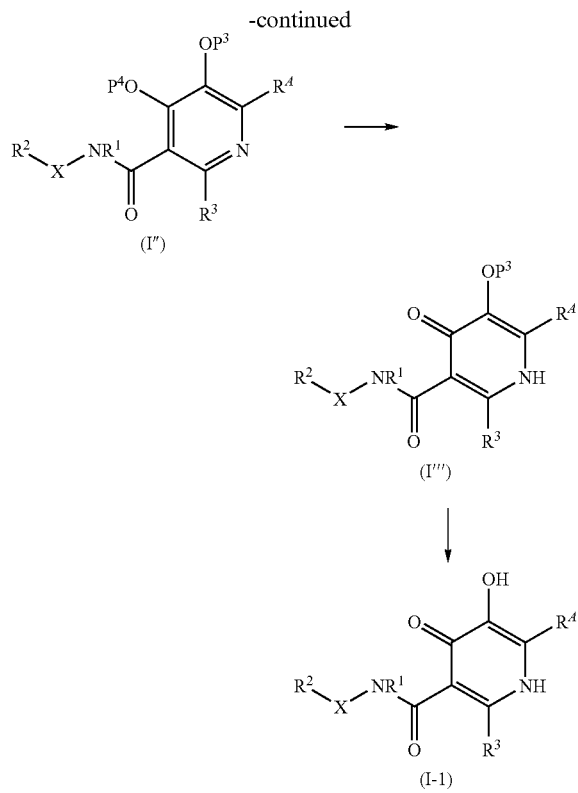

(wherein $P^1$ is a hydroxy protecting group; $P^3$ is hydrogen or a hydroxy protecting group; $P^4$ is a hydroxy protecting group; other symbols are as defined above)

A preferable aspect of Compound (I'), (I") or (I''') will be explained below.

Each hydroxy protecting group is preferably lower alkyl (e.g. methyl, ethyl) or aralkyl (e.g. benzyl).

$R^1$ is preferably hydrogen or lower alkyl, particularly preferably hydrogen.

X is preferably lower alkylene, more preferably $C_1$-$C_3$ lower alkylene, particularly preferably methylene.

$R^2$ is preferably optionally substituted phenyl, more preferably phenyl, or phenyl substituted at least with halogen (e.g. 4-F-phenyl).

$R_3$ is preferably hydrogen.

$R_4$ is preferably a group represented by the formula: —$COR_5$ ($R_5$ is a group selected from the substituent group A). More preferably, $R_5$ is hydrogen, hydroxy, or lower alkyl.

Y is preferably $NR_4$ (wherein $R_4$ is preferably hydrogen, or optionally substituted lower alkyl). A substituent in optionally substituted lower alkyl of $R_4$ is preferably —CH=$CH_2$, —CHO etc. $R_4$ is more preferably hydrogen, —$CH_2$CH=$CH_2$, —$CH_2$CHO, etc.

An aspect of Compounds (I') and (I''') includes the Compounds (XI) and (XIV).

An aspect of Compound (I") includes the Compounds (X), (XII), (XIII), (XV) and (XVI).

The present compound is useful as a drug such as an antivirus drug and the like. The present compound has the remarkable inhibitory activity against integrase of a virus. Therefore, the present compound can be expected to have the preventing or treating effect for various diseases resulting from a virus which is proliferated by producing at least integrase at infection in an animal cell, is useful as an integrase inhibitor against retrovirus (e.g. HIV-1, HIV-2, HTLV-1, SIV, FIV etc.), and is useful as an anti-HIV drug or the like.

Alternatively, the present compound can be also used in joint use therapy by combining with an anti-HIV drug having different mechanism of action such as a reverse transcriptase inhibitor and/or a protease inhibitor. Particularly, currently, an integrase inhibitor is not sold on the market, and it is useful to combine the present compound and a reverse transcriptase inhibitor and/or a protease inhibitor to use in joint use therapy.

Further, the aforementioned use includes not only use as an anti-HIV medical mixture, but also use as a joint use agent for enhancing the anti-HIV activity of other anti-HIV drug such as cocktail therapy.

In addition, the present compound can be used for preventing infection with a retrovirus vector from spreading into tissues other than an objective tissue, when a retrovirus vector based on HIV or MLV is used in the field of gene therapy. Particularly, in the case where a cell is infected with a vector in vitro, and this is returned into a body, when the present compound is administered in advance, unnecessary infection can be prevented in vivo.

The present compound can be administered orally or parenterally. When orally administered, the present compound can be used as a conventional preparation, for example, as any dosage form of solid preparations such as tablets, powders, granules, capsules and the like; solutions ; oil suspensions; liquids preparations such as syrups or elixirs. When parenterally administered, the present compound can be used as aqueous or oily suspension injectables, or nasal drops. Upon production of preparations, conventional excipients, binders, lubricants, aqueous solvents, oily solvents, emulsifiers, suspending agents, preservatives, stabilizers and the like can be arbitrarily used. As an anti-HIV drug, particularly, an oral preparation is preferable. Preparations of the present invention can be produced by combining (e.g. mixing) a therapeutically effective amount of the present compound with a pharmaceutically acceptable carrier or diluent.

A dose of the present compound is different depending on an administration method, an age, a weight and condition of a patient, and a kind of a disease. Usually, in the case of oral administration, the present compound may be administered at an amount of about 0.05 mg to 3000 mg, preferably about 0.1 mg to 1000 mg per adult a day by, if necessary, dividing the dose. In addition, in the case of parenteral administration, the present compound is administered at an amount of about 0.01 mg to 1000 mg, preferably about 0.05 mg to 500 mg per adult a day.

EXAMPLES (Abbreviations)

Me=methyl; Bn=benzyl

Examples A-1

[Chemical formula 12]

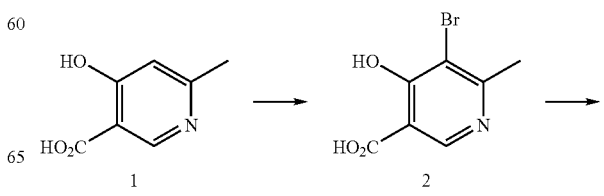

-continued

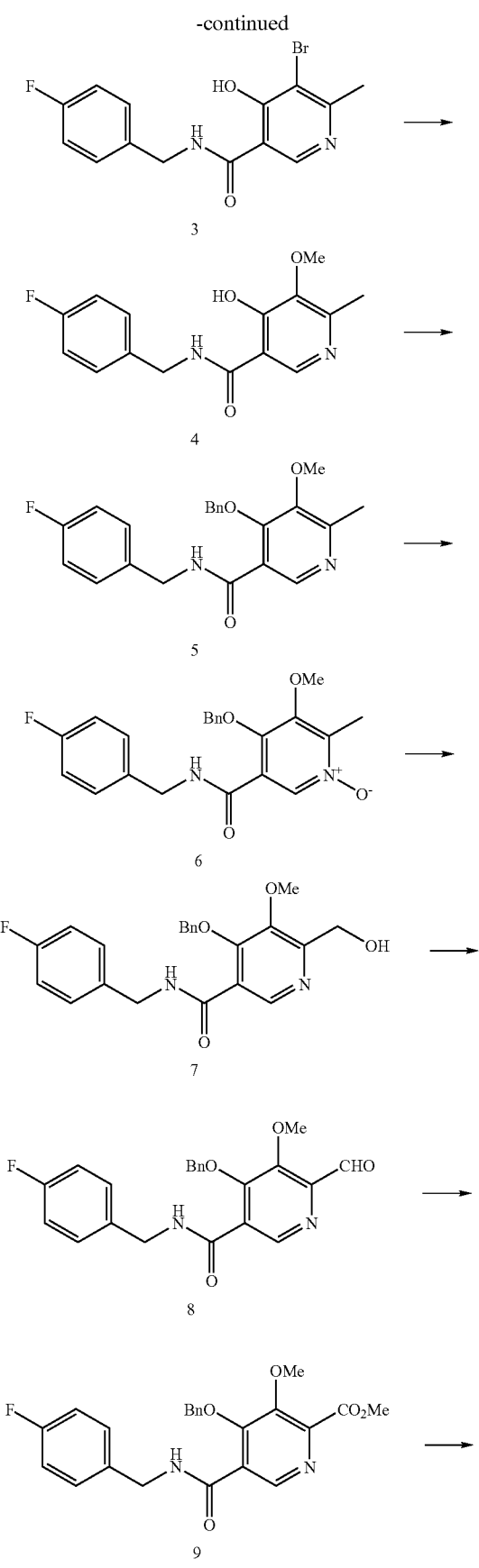

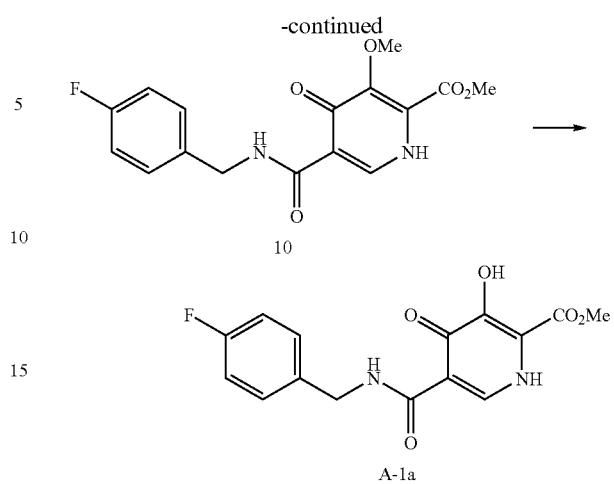

A-1a. Methyl 5-(4-fluorobenzylcarbamoyl)-3-hydroxy-4-oxo-1,4-dihydropyri dine-2-carboxylate 1) 4-Hydroxy-6-methylnicotinic acid 1 (95.6 g, 0.625 mol) was dissolved in acetic acid (950 ml) and water (190 ml), and bromine (39 ml, 0.750 mol) was added over 15 minutes. After the solution was stirred at 60° C. for 5 hours, a solvent was distilled off under reduced pressure, methanol (200 ml) was added, and crystals were collected by filtration. The solution was distilled off under reduced pressure, methanol was added again to the residue, and crystals were collected by filtration. Crystals were combined to obtain 142.2 g (98%) of 5-bromo-4-hydroxy-6-methylnicotinic acid 2 as a colorless crystal.

NMR(DMSO-$d_6$)d: 2.53 (3H, s), 8.56 (1H, s), 13.45 (1H, br s), 14.80 (1H, br s).

2) The compound 2 (138 g, 0.596 mol), 1-ethyl-3-(3-dimethylaminopropyl)carbodiimide hydrochloride (148 g, 0.775 mol), and 1-hydroxybenzotriazole (100 g, 0.656 mol) were dissolved in dimethylformamide (970 ml), and 4-fluorobenzylamine (79 ml, 0.715 mol) was added. The reaction solution was stirred at room temperature for 9 hours, water (2 liter) was added, and crystals were collected by filtration, and washed with ether. 5-Bromo-N-(4-fluorobenzyl)-4-hydroxy-6-methylnicotineamide 3 (156 g, 77%) was obtained as a colorless crystal.

NMR(DMSO-$d_6$)d: 2.47 (3H, s), 4.50 (2H, d, J=5.9 Hz), 7.12-7.20 (m, 2H), 7.32-7.39 (m, 2H), 8.38 (1H, s), 10.50 (1H, t, J=5.9 Hz), 12.72 (1H, br s).

3) The compound 3 (75.2 g, 222 mmol) and copper (I) iodide (21.1 g, 111 mmol) were dissolved in dimethylformamide (750 ml), a 28% sodium methoxide-methanol solution (216 ml, 888 mmol) was added, and the mixture was stirred at 105° C. for 100 minutes. After cooling, ice water (800 ml) was added, and undesired substances were filtered off. 2M hydrochloric acid (443 ml) was added to the solution, and crystals were collected by filtration. N-(4-fluorobenzyl)-4-hydroxy-5-methoxy-6-methylnicotineamid e 4 (56.0 g, 87%) was obtained as a colorless crystal.

NMR(DMSO-$d_6$)d: 2.26 (3H, s), 3.74 (3H, s), 4.49 (2H, d, J=6.0 Hz), 7.10-7.19 (2H, m), 7.30-7.38 (2H, m), 8.24 (1H, s), 10.68 (1H, t, J=6.0 Hz), 12.21 (1H, br s).

4) To a solution of the compound 4 (100 g, 344 mmol), benzyl alcohol (46 ml, 447 mmol) and tributylphosphine (128 ml, 516 mmol) in tetrahydrofuran (1.0 liter) was added a 40% azodicarboxylic acid diisopropyl-toluene solution (280 ml, 516 mmol) over 30 minutes under ice-cooling. After stirred for 30 minutes under ice-cooling, a temperature was raised to room temperature, and the mixture was stirred further for 2 hours. The solvent was distilled off under reduced pressure, toluene (100 ml) and hexane (2 liter) were added to the residue, and precipitated crystals were filtered off. Te solvent was distilled off under reduced pressure, diethyl ether (200 ml) and hexane (2 liter) were added to the residue, and precipitated crystals were filtered off. The solvent was distilled off under reduced pressure, and the residue was purified by silica gel column chromatography (hexane/ethyl acetate). 4-Benzyloxy-N-(4-fluorobenzyl)-5-methoxy-6-methylnicotineamide 5 (68.5 g, 52%) was obtained as a colorless crystal.

NMR (CDCl$_3$)d: 2.58 (3H, s), 3.86 (3H, s), 4.40 (2H, d, J=5.7 Hz), 5.21 (2H, s), 6.91-7.00 (2H, m), 7.08-7.14 (2H, m), 7.19-7.27 (2H, m), 7.32-7.40 (3H, m), 7.87 (1H, br s), 8.97 (1H, s).

5) To a solution of the compound 5 (67.5 g, 177 mmol) in chloroform (350 ml) was added a solution of metachloroperbenzoic acid (65%) (49.5 g, 186 mmol) in chloroform (350 ml) over 30 minutes under ice-cooling. After stirred for 45 minutes under ice-cooling, a temperature was raised to room temperature, and the solution was stirred for 75 minutes. To the reaction solution was added an aqueous saturated sodium bicarbonate solution, and this was extracted with chloroform. The organic layer was washed with an aqueous saturated sodium bicarbonate solution, and dried with anhydrous sodium sulfate. The solvent was distilled off under reduced pressure, diethyl ether (200 ml) was added to the residue, and precipitated crystals (47.8 g) were collected by filtration. The solvent was distilled off under reduced pressure, and the residue was purified by silica gel column chromatography (toluene/acetone) to obtain 2.65 g of crystals. Crystals were combined to obtain 50.5 g (72%) of 4-benzyloxy-N-(4-fluorobenzyl)-5-methoxy-6-methyl-4-oxynicotineamide 6 as a colorless crystal.

NMR (CDCl$_3$) d: 2.55 (3H, s), 3.90 (3H, s), 4.40 (2H, d, J=5.7 Hz), 5.16 (2H, s), 6.93-6.70 (2H, s), 6.90-7.19 (5H, m), 7.30-7.38 (2H, m), 7.94 (1H, br s), 8.81 (1H, s).

6) The compound 6 (49.4 g, 125 mmol) was dissolved in acetic anhydride (350 ml), and stirred at 80° C. for 30 minutes. The solvent was distilled off under reduced pressure, the residue was dissolved in methanol (500 ml), a 28% sodium methoxide-methanol solution (7.5 ml, 31.3 mmol) was added under ice-cooling, and the mixture was stirred at room temperature for 1 hour. Amberlite (registered trade mark) IR-120B was added to the reaction solution until the solution became neutral, and the solid was filtered off. The solvent was distilled off under reduced pressure, and the residue was purified by silica gel column chromatography (hexane/ethyl acetate). 4-Benzyloxy-N-(fluorobenzyl)-6-hydroxymethyl-5-methoxynicotineamide 7 (25.4 g, 51%) was obtained as a colorless crystal.

NMR (CDCl$_3$) d: 3.42 (1H, br s), 3.89 (3H, s), 4.41 (2H, d, J=5.7 Hz), 4.83 (2H, s), 5.23 (2H, s), 6.92-6.99 (2H, m), 7.09-7.14 (2H, m), 7.19-7.23 (2H,m)., 7.28-7.37 (3H, m), 7.85 (1H, brs), 9.03 (1H, s).

7) To a solution of the compound 7 (25.0 g, 63.1 mmol), dimethyl sulfoxide (44.8 ml, 631 mmol) and triethylamine (44.3 ml, 378 mmol) in chloroform (250 ml) was added sulfur trioxide pyridine complex (50.2 g, 315 mmol) under ice-cooling, and the mixture was stirred at room temperature for 20 minutes. To the reaction solution was added water, chloroform was distilled off under reduced pressure, and the residue was extracted with ethyl acetate. The extract was washed with water, and dried with anhydrous sodium sulfate. The solvent was distilled off under reduced pressure, diethyl ether was-added to the residue, and crystals (17.7 g) were collected by filtration. The solvent was distilled off under reduced pressure, and the residue was purified by silica gel column chromatography to obtain 3.16 g of crystals. Crystals were combined to obtain 20.9 g (84%) of 4-benzyloxy-N-(4-fluorobenzyl)-6-formyl-5-methoxynicotineamide 8 was obtained as a colorless crystal.

NMR (CDCl$_3$) d: 4.02 (3H, s), 4.41 (2H, d, J=5.7 Hz), 5.30 (2H, s), 6.93-6.70 (2H, m), 7.09-7.15 (2H, m), 7.20-7.27 (2H, m), 7.31-7.40 (3H, m), 7.83 (1H, br s), 9.20 (1H, s), 10.26 (1H, s).

8) To a solution of the compound 8 (300 mg, 0.761 mmol) in methanol (1 ml) was added a solution of potassium hydroxide (111 mg, 1.99 mmol) in methanol. (1 ml) under ice-cooling, a solution of iodine (251 mg, 1.00 mmol) in methanol (4 ml) was added, and the mixture was stirred at the same temperature for 1 hour. To the reaction solution were added a 5% aqueous sodium hydrogen sulfite solution and water, and precipitated crystals were collected by filtration. Methyl 4-benzyloxy-5-(4-fluorobenzylcarbamoyl)-3-methyoxypyridine-2-carboxylate 9 (275 mg, 85%) was obtained as a colorless crystal.

NMR (CDCl$_3$) d: 3.99 (3H, s), 4.02 (3H, s), 7.40 (2H, d, J=5.7 Hz), 5.26 (2H, s), 6.92-6.99 (2H, m), 7.10-7.15 (2H, m), 7.19-7.23 (2H, m), 7.25-7.39 (3H, m), 7.81 (1H, br s), 9.09 (1H, s).

9) To a suspension of sodium iodide (5.51 g, 36.8 mmol) in acetonitrile (50 ml) was added chlorotrimethylsilane (4.66 ml, 36.8 mmol), and the mixture was stirred at room temperature for 10 minutes. To this solution was added the compound 9 (2.60 g, 6.13 mmol) under ice-cooling, and the mixture was stirred at the same temperature for 20 minutes. To the reaction solution was added a 5% sodium hydrogen sulfite solution, followed by extraction with ethyl acetate. The extract was washed with an aqueous saturated sodium bicarbonate solution and an aqueous saturated sodium chloride solution, and dried with anhydrous sodium sulfate. The solvent was distilled off under reduced pressure, and the resulting solid was recrystallized (acetone-diisopropyl ether), to obtain methyl 5-(4-fluorobenzylcarbamoyl)-3-methoxy-4-oxo-1,4-dihydropyridine-2-carboxylate 10 (1.73 g, 84%) as a colorless crystal.

NMR (CDCl$_3$) d: 4.04 (6H, s), 4.60 (2H, d, J=6.0 Hz), 6.96-7.03 (2H, m), 7.29-7.35 (2H, m), 8.63 (1H, s), 9.68 (1H, br s), 10.34 (1H, br s).

10) To a solution of the compound 10 (1.73 g, 5.17 mmol) in dichloromethane (150 ml) was added aluminum chloride (6.97 g, 51.7 mmol), and the mixture was stirred at room temperature for 2 hours. The reaction solution was poured into 2M hydrochloric acid containing an ice, followed by extraction with ethyl acetate. The extract was washed with 2M hydrochloric acid and water, and dried with anhydrous sodium sulfate. The solvent was distilled off under reduced pressure, and the resulting solid was recrystallized (tetrahydrofuran-methanol) to obtain Compound A-1a (919 mg, 56%) as a colorless crystal.

Melting point: 242-244° C.

Elementary analysis: for $C_{15}Hl_3FN_2O_5$

Cal'd (%): C, 56.25; H, 4.09; F, 5.93; N, 8.75.

Found (%): C, 56.00; H, 4.03; F, 5.58; N, 8.69.

NMR (DMSO-$d_6$) d:3.91 (3H, s),4.52 (2H, d, J=5.8 Hz), 7.12-7.19 (2H, m), 7.34-7.40 (2H, m), 8.19-8.22 (1H, m), 10,12 (1H, br s), 10.20 (1H, d, J=5.8 Hz), 12.43 (1H, br s).

Example A-2

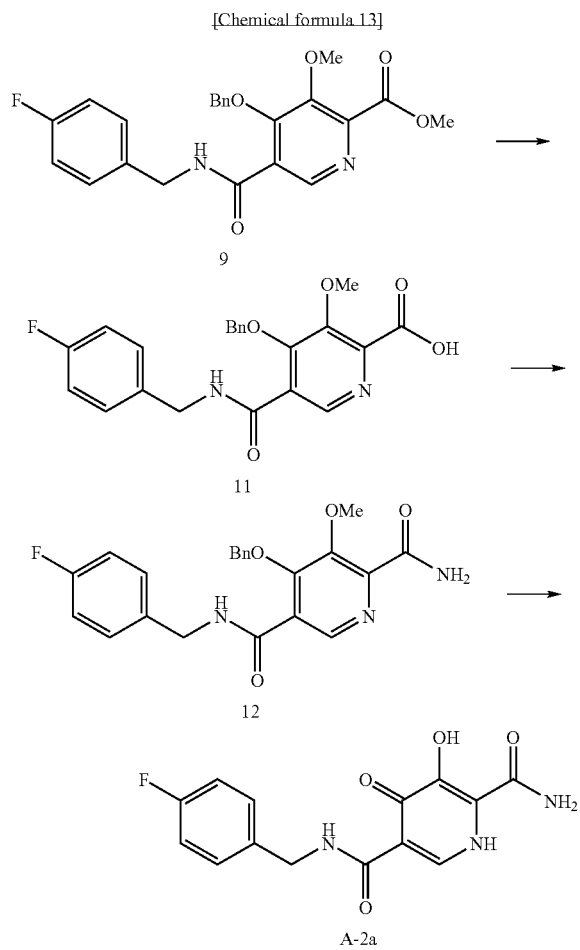

1) 9 (900 mg, 2.12 mmol) was dissolved in methanol (8 ml), and a 2N aqueous sodium hydroxide solution (4 ml) was added. The solution was stirred at room temperature for 2 hours, 2M hydrochloric acid (3 ml) was added, and crystals were filtered off. 4-Benzyloxy-5-(4-fluoro-benzylcarbamoyl)-3-methoxy-pyridine-2-carboxylic acid 11 (474 mg, 54%) was obtained as a colorless crystal.

NMR (CDCl$_3$) d: 4.05 (3H, s), 4.40 (2H, d, J=5.6 Hz), 5.36 (2H, s), 6.94-7.01 (2H, m), 7.08-7.12 (2H, m), 7.21-7.24 (2H, m), 7.29-7.41 (3H, m), 7.87 (1H, brs), 9.03 (1H, s).

2) The compound 11 (155 mg, 0.378 mmol), 2-ethyl-3-(3-dimethylaminopropyl) carbodiimide hydrochloride (87 mg, 0.453 mmol), and 1-hydroxybenzotriazole (61 mg, 0.453 mmol) were dissolved in dimethylformamide (2 ml), and the solution was stirred at room temperature for 30 minutes. Thereafter, ammonium chloride (40 mg, 0.756 mmol), and diisopropylethylamine (198 μl, 1.13 mmol) were added. The reaction solution was stirred at room temperature for 1 hour, water was added, and crystals were collected by filtration, and washed with ether. 4-Benzyloxy-3-methoxy-pyridine-2,5-dicarboxylic acid 2-amide 5-(4-fluoro-benzylamide) 12 (127 mg, 82%) was obtained as a colorless crystal.

3) To the compound 12 (127 mg, 0.310 mmol) was added pyridinium chloride (1.27 g.), and the mixture was heated at 180° C. for 5 minutes. After cooling, water was added, crystals were collected by filtration, and washed with ether. 3-Hydroxy-4-oxo-1,4-dihydro-pyridine-2,5-dicarboxylic acid 2-amide 5-(4-fluoro-benzylamide) A-2a (88 mg, 93%) was obtained as a skin-colored crystal.

Melting point: 300° C. or higher

Elementary analysis: for $C_{14}H_{12}FN_3O_4$

Cal'd (%): C, 55.08; H, 3.96; F, 6.22; N, 13.77.

Found (%): C, 54.82; H, 3.96; F, 5.75; N, 13.53; Cl, 0.79.

NMR (DMSO-$d_6$) d: 4.53 (2H, d, J=5.6 Hz), 7.14-7.20 (2H, m), 7.35-7.40 (2H, m), 7.79 (1H, s), 8.24 (1H, d, J=7.0 Hz), 8.33 (1H, s), 10.33 (1H, t, J=5.6 Hz), 12.23 (1H, d, J=7.0 Hz).

The following compounds were synthesized by the similar method.

A-2b 3-hydroxy-4-oxo-1,4-dihydro-pyridine-2,5-dicarboxylic acid 5-(4-fluoro-benzylamide) 2-methylamide Melting point: 300° C. or higher Elementary analysis: for $C_{15}H_{14}FN_3O_4$ Cal'd (%): C, 56.43; H, 4.42; F, 5.95; N, 13.16.

Found (%): C, 56.18; H, 4.36; F, 5.63; N, 12.96.

NMR (DMSO-$d_6$) d: 2.91 (3H, d, J=4.7 Hz), 4.53 (2H, d, J=5.8 Hz), 7.14-7.20 (2H, m), 7.35-7.40 (2H, m), 8.23-8.25 (1H, m), 8.35 (1H, d, J=5.0 Hz), 10.35 (1H, t, J=5.8 Hz), 12.23 (1H, d, J=6.3 Hz).

A-2c 3-Hydroxy-4-oxo-1,4-dihydro-pyridine-2,5-dicarboxylic acid 2-dimethylamide 5-(fluoro-benzylamide)

Melting point: 269-270° C.

Elementary analysis: for $C_{16}H_{16}FN_3O_4$

Cal'd (%): C, 57.65; H, 4.84; F, 5.70; N, 12.61.

Found (%): C, 57.44; H, 4.79; F, 5.40; N, 12.41; Cl, 0.59.

NMR (DMSO-$d_6$) d: 2.92 (3H, s), 3.00 (3H, s), 4.53 (2H, d, J=5.8 Hz), 7.13-7.19 (2H, m), 7.34-7.39 (2H, m), 8.19-8.21 (1H, m), 9.63 (1H, brs), 10.44 (1H, t, J=5.8 Hz), 12.60 (1H, brs).

Example A-2d

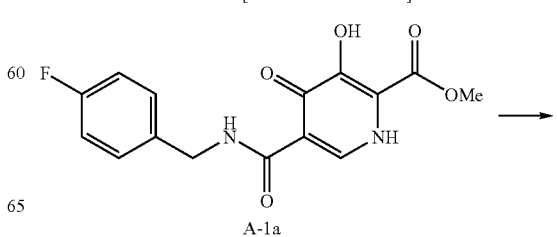

-continued

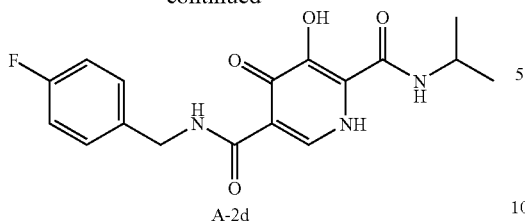

A-2d

1) A-1a (100 mg, 0.3 mmol) was dissolved in methanol (1 ml)., and a reaction was performed with a microwave reaction apparatus at 140° C. for 15 minutes. After cooled to room temperature, 2N hydrochloric acid (3 ml) was added, the mixture was, stirred, and precipitated crystals were collected by filtration. 3-Hydroxy-4-oxo-1,4-dihydro-pyridine-2,5-dicarboxylic acid 5-(4-fluoro-benzylamide) 2-isopropylamide A-2d (93 mg, 86%) was obtained as a colorless crystal.

Melting point: 295-299° C.

NMR (DMSO-$d_6$) d:1.21 (6H, d, J=6.6 Hz),4.06-4.15 (1H, m),4.53 (2H, d, J=5.8 Hz), 7.13-7.21 (2H, m), 7.35-7.40 (2H, m), 8.16 (1H, d, J=7.6 Hz), 8.24 (1H, d, J=7.0 Hz), 10.33 (1H, t, J=5.7 Hz), 12.24 (1H, d, J=5.5 Hz).

The following compounds were synthesized by the similar method.

A-2e 3-Hydroxy-4-oxo-1,4-dihydro-pyridine-2,5-dicarboxylic acid 5-(4-fluoro-benzylamide) 2-[(2-methoxy-ethyl) amide]

Melting point:295-299° C.

NMR (DMSO-$d_6$) d: 3.28 (3H, s), 3.39-3.62 (4H, m), 4.52 (2H, d, J=5.9 Hz), 7.14-7.20 (2H, m), 7.35-7.39 (2H, m), 8.24 (1H, d, J=7.2 Hz), 8.46 (1H, t, J=5.2 Hz), 10.32 (1H, t, J=5.8 Hz), 12.23 (1H, d, J=5.8 Hz).

A-2f 3-Hydroxy-4-oxo-1,4-dihydro-pyridine-2,5-dicarboxylic acid 5-(4-fluoro-benzylamide) 2-[(2-hydroxy-ethyl)-amide]

Melting point: 285-287° C.

NMR (DMSO-$d_6$) d: 3.44-3.61 (4H, m), 4.53 (2H, d, J=6.0 Hz),4.91 (1H, s), 7.13-7.21 (2H, m), 7.35-7.40 (2H, m), 8.24 (1H, s), 8.53 (1H, s), 10.34 (1H, t, J=5.7 Hz), 12.23 (1H, brs).

A-2g 3-Hydroxy-4-oxo-1,4-dihydro-pyridine-2,5-dicarboxylic acid 5-(4-fluoro-benzylamide)

2-[((thiophene-2-ylmethyl)amide]

Melting point: 297-300° C.

NMR (DMSO-$d_6$) d: 4.53 (2H, d, J=5.6 Hz), 4.75 (2H, d, J=5.8 Hz), 6.96-6.99 (1H, m), 7.06-7.07 (1H, m), 7.14-7.21 (2H, m), 7.35-7.44 (3H, m), 8.24 (1H, d, J=7.0 Hz), 8.88 (1H, t, J=6.0 Hz), 10.33 (1H, t, J=5.7 Hz), 12.32 (1H, d, J=6.3 Hz).

A-2h 3-Hydroxy-4-oxo-1,4-dihydro-pyridine-2,5-dicarboxylic acid bis-(4-fluoro-benzylamide)

Melting point: 279-280° C.

NMR (DMSO-$d_6$) d: 4.53 (2H, d, J=5.6 Hz), 4.57 (2H, d, J=6.0 Hz), 7.14-7.20 (4H, m), 7.36-7.42 (4H, m), 8.24 (1H, d, J=7.1 Hz), 8.85 (1H, t, J=6.4 Hz), 10.34 (1H, t, J=5.9 Hz), 12.28 (1H, d, J=7.0 Hz).

A-2i 3-Hydroxy-4-oxo-1,4-dihydro-pyridine-2,5-dicarboxylic acid 5-(4-fluoro-benzylamide)

2-[(3-imidazol-1-yl-propyl)-amide]

NMR (DMSO-$d_6$) d: 2.07-2.16 (2H, m),3.40 (2H, q, J=6.6 Hz),4.26 (2H, t, J=7.1 Hz), 4.53 (2H, d, J=5.6 Hz), 7.14-7.22 (2H, m), 7.34-7.40 (2H, m), 7.7.0-7.71 (1H, m), 7.83-7.84 (1H, m), 9.18 (1H, s), 10.34 (1H, t, J=5.8 Hz), 12.29 (1H, brs), 14.74 (1H, brs).

A-2j 3-Hydroxy-4-oxo-1,4-dihydro-pyridine-2,5-dicarboxylic acid 2-cyclohexylamide 5-(4-fluoro-benzylamide)

Melting point: 290-293° C.

NMR (DMSO-$d_6$) d: 1.24-1.89 (10H, m), 3.85-3.87 (1H, m), 4.53 (2H, d, J=5.6 Hz), 7.13-7.20 (2H, m), 7.34-7.40 (2H, m), 8.23-8.26 (2H, m), 10.33 (1H, t, J=5.6 Hz), 12.24 (1H, d, J=7.3 Hz).

A-2k 3-Hydroxy-4-oxo-1,4-dihydro-pyridine-2,5-dicarboxyl acid 5-(4-fluoro-benzylamide)

2-{[3-(2-oxo-pyrrolidine-1-yl)-propyl]-amide}

Melting point: 248-252° C.

NMR (DMSO-$d_6$) d: 1.72 (2H, t, J=6.9 Hz), 1.93 (2H, q, J=7.5 Hz), 2.22 (2H, t, J=8.0 Hz), 3.22 (2H, t, J=6.9 Hz), 3.30-3.37 (4H, m), 4.53 (2H, d, J=5.6 Hz), 7.14-7.20 (2H, m), 7.35-7.40 (2H, m), 8.23-8.25 (1H, m), 8.49 (1H, t, J=6.0 Hz), 10.35 (1H, t, J=5.8 Hz), 12.23 (1H, d, J=7.3 Hz).

A-2l 3-Hydroxy-4-oxo-1,4-dihydro-pyridine-2,5-dicarboxylic acid 5-(4-fluoro-benzylamide) 2-[(2-phenoxy-ethyl)-amide]

Melting point: 279-282° C.

NMR (DMSO-$d_6$) d: 3.74-3.80 (2H, m), 4.12-4.16 (2H, d, J=5.5 Hz), 4.50-4.53 (2H, m), 6.92-7.00 (3H, m), 7.13-7.20 (3H, m), 7.27-7.40 (4H, m), 8.24 (1H, s), 8.70 (1H, s), 10.34 (1H, t, J=5.6 Hz), 12.24 (1H, brs).

A-2m 3-Hydroxy-4-oxo-1,4-dihydro-pyridine-2,5-dicarboxylic acid 2-{[2-(4-chloro-phenyl)-ethyl]-amide}

5-(4-fluoro-benzylamide)

Melting point: 241-245° C.

NMR (DMSO-$d_6$) d: 2.86 (2H, t, J=7.1 Hz), 3.61 (2H, q, J=6.4 Hz), 4.53 (2H, d, J=5.6 Hz), 7.14-7.20 (2H, m), 7.27-7.40 (6H, m), 8.23 (1H, d, J=7.2 Hz), 8.45 (1H, t, J=5.9 Hz), 10.34 (1H, t, J=5.8 Hz), 12.23 (1H, d, J=7.0 Hz).

A-2n 3-Hydroxy-4-oxo-1,4-dihydro-pyiridine-2,5-dicarboxylic acid 2-[(S)-1-cyclohexyl-ethyl]-amide]

5-(4-fluoro-benzylamide)

Melting point: 262-264° C.

NMR (DMSO-$d_6$) d: 0.92-1.77 (10H, m), 3.90-3.97 (1H, m), 4.53 (2H, d, J=5.6 Hz),7.13-7.21 (2H, m),7.35-7.40 (2H, m), 8.17-8.25 (2H, m), 10.33 (1H, t, J=6.1 Hz), 12.23 (1H, d, J=5.8 Hz).

A-2o 3-Hydroxy-4-oxo-1,4-dihydro-pyridine-2,5-dicarboxylic acid 5-(4-fluoro-benzylamide) 2-indone-1-ylamide Melting point: 237-240° C.
NMR (DMSO-$d_6$) d:1.89-1.96 (1H, m), 2.55-2.60 (1H, m), 2.86-3.00 (2H, m), 4.53(2H, d, J=5.6 Hz), 5.55-5.58 (1H, m), 7.14-7.40 (8H, m), 8.27 (1H, d, J=6.6 Hz), 8.55 (1H, d, J=8.1 Hz), 10.32 (1H, t, J=5.8 Hz), 12.35 (1H, d, J=5.8 Hz).

A-2p 3-Hydroxy-4-oxo-1,4-dihydro-pyridine-2,5-dicarboxylic acid 2-[(2-cyclohex-1-enyl-ethyl)-amide]

5-(4-fluoro-benzylamide)

Melting point: 251-253° C.
NMR (DMSO-$d_6$) d: 1.48-1.59 (4H, m),1.94-1.95 (4H, m), 2.14-2.19 (2H, m), 3.42-3.49 (2H, m), 2.91 (3H, d, J=4.7 Hz), 4.53 (2H, d, J=5.6 Hz), 5.46 (1H, s), 7.14-7.20 (2H, m), 7.35-7.40 (2H, m), 8.24 (1H, d, J=7.0 Hz), 8.36 (1H, d, J=5.6 Hz), 10.35 (1H, t, J=5.6 Hz), 12.23 (1H, d, J=7.3 Hz).

Example A-3

[Chemical formula 14]

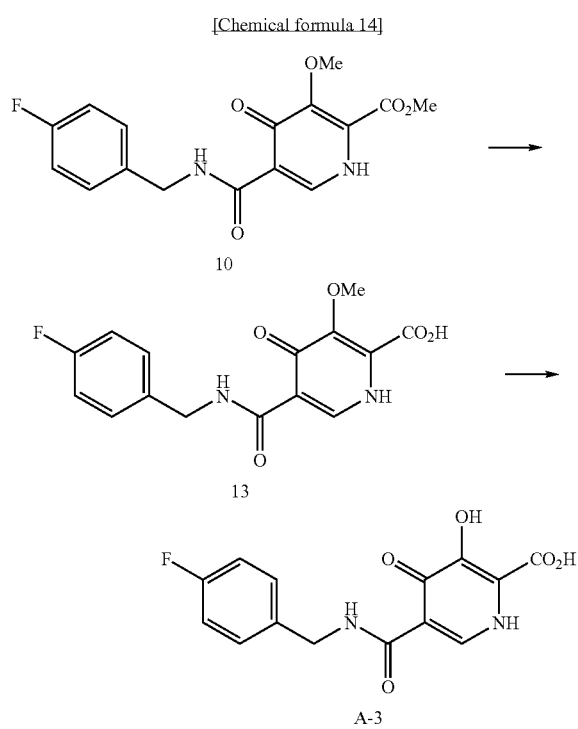

1) To a solution of Compound 10 (4.8 g, 14 mmol) in methanol (60 ml) was added a 2N aqueous lithium hydroxide solution (30 ml) under ice-cooling. After stirred at room temperature for 1.5 hours, 2N hydrochloric acid was slowly added until acidic. Precipitated crystals were washed with water, and dried to obtain Compound 13 (3.75 g).
2) To a solution of Compound 13 (200 mg, 0.624 mmol) in dichloromethane (4 ml) was added a 1.0 M boron tribromide dichloromethane solution (3.1 ml, 3.10 mmol), and the mixture was stirred at room temperature for 3 hours and 30 minutes. The reaction solution was poured into ice water, 2 M hydrochloric acid was added, and this was extracted with ethyl acetate. The extract was washed with water, and dried with anhydrous sodium sulfate. The solvent was distilled off under reduced pressure, and the residue was washed with a mixed solution of ethyl acetate-methanol to obtain Compound A-3 as a colorless crystal (35 mg).

NMR (DMSO-$d_6$) d: 4.51 (2H, d, J=5.7 Hz), 7.12-7.19 (2H, m), 7.33-7.39 (2H, m), 8.17 (1H, s).

The present invention also includes the following compounds.

[Chemical formula 15]

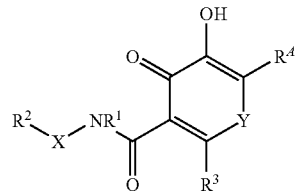
(I)

$R^1$: hydrogen or methyl $R^2$-X:

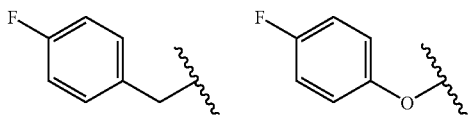

$R^3$: hydrogen

Y: >NH, >NMe, >NPh, >NBn, >O $R^4$:

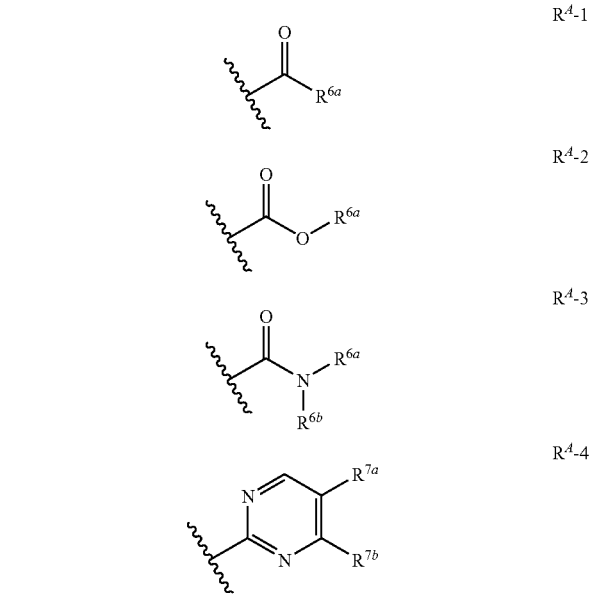

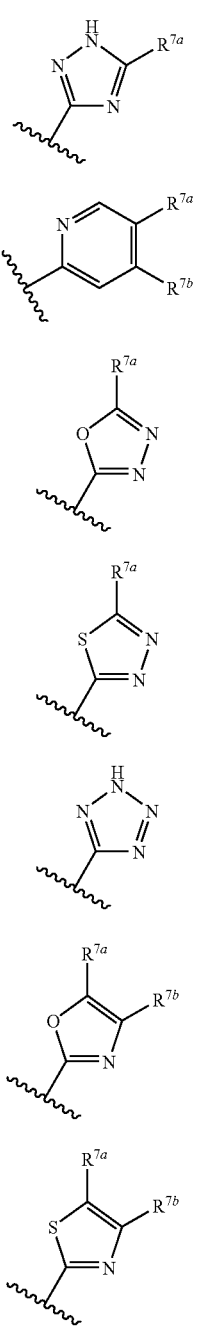

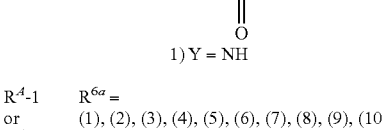

R⁶ᵃ, R⁶ᵇ: (1)hydrogen, (2)methyl, (3)ethyl, (4)n-propyl, (5) isopropyl, (6)2-hydroxyethyl,(7)2-methoxyethyl, (8)phenyl, (9) benzyl, (10) morpholine, (11)1,1-dimethylhydrazine (12)O-methylhydroxylamine, (13)4-fluorobenzyl, (14)4-fluorophenyloxy, (15)4-fluorobenzyloxy R⁷ᵃ, R⁷ᵇ: (1)hydrogen, (2)methyl, (3)ethyl, (4)n-propyl, (5) isopropyl, (6) 2-hydroxyethyl, (7) 2-methoxyethyl, (8) phenyl, (9) benzyl, (10) morpholine, (11) 1,1-dimethylhydrazine, (12) O-methylhydroxylamine, (13) halogen, (F, Cl, Br, I) (14) hydroxy, (15) acetyl, (16) methoxycarbonyl, (17) carbamoyl, (18) 4-fluorobenzyl, (19) 4-fluorophenyloxy, (20) 4-fluorobenzyloxy

| No | $R^A$ | $R^6, R^7$ |
|---|---|---|
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1, |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 18]

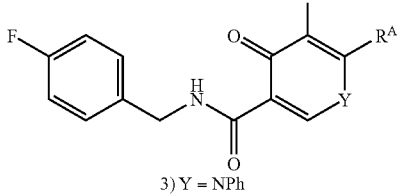

3) Y = NPh

| No | $R^A$ | $R^6, R^7$ |
|---|---|---|
| 1-1 | $R^A$-1 | $R^{6a}=$ |
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1, |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 19]

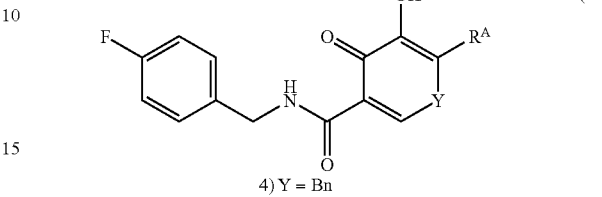

4) Y = Bn

| No | $R^A$ | $R^6, R^7$ |
|---|---|---|
| 1-1 | $R^A$-1 | $R^{6a}=$ |
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1, |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 20]

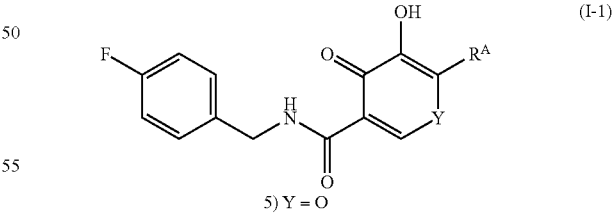

5) Y = O

| No | $R^A$ | $R^6, R^7$ |
|---|---|---|
| 1-1 | $R^A$-1 | $R^{6a}=$ |
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |

| No | $R^A$ | $R^6, R^7$ |
|---|---|---|
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}$ = |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}$= |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

| No | $R^A$ | $R^6, R^7$ |
|---|---|---|

[Chemical formula 21]

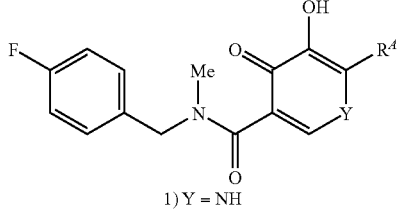

(I-2)

1) Y = NH

| 1-1 | $R^A$-1 | $R^{6a}$ = |
|---|---|---|
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}$ = |
| | | (1, 1), (1, 2), (1, 3), (1, 4), (1, 5), (1, 6), (1, 7), |
| | | (1, 8), (1, 9), (1, 10), (1, 11), (1, 12), (1, 13), |
| | | (1, 14), (1, 15) |
| | | (2, 2), (2, 3), (2, 4), (2, 5), (2, 6), (2, 7), (2, 8). |
| | | (2, 9), (2, 10), (2, 11), (2, 12), (2, 13), (2, 14), |
| | | (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15), |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}$ = |
| 1-6 | $R^A$-6 | (1, 1), (1, 2), (1, 3), (1, 4), (1, 5), (1, 6), (1, 7), |
| 1-10 | $R^A$-10 | (1, 8), (1, 9), (1, 10), (1, 11), (1, 12), (1, 13), |
| 1-11 | or | (1, 14), (1, 15), (1, 16), (1, 17), (1, 18), (1, 19) |
| | $R^A$-11 | (1, 20),, |
| | | (2, 1), (3, 1), (4, 1), (5, 1), (6, 1), (7, 1), (8, 1), |
| | | (9, 1), (10, 1), (11, 1), (12, 1), (13, 1), (14, 1), |
| | | (15, 1), (16, 1), (17, 1), (18, 1), (19, 1), (20, 1), |
| | | (2, 2), (2, 3), (2, 4), (2, 5), (2, 6), (2, 7), (2, 8), |
| | | (2, 9), (2, 10), (2, 11), (2, 12), (2, 13), (2, 14), |
| | | (2, 15), (2, 16), (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), (3, 15), |
| | | (3, 16), (3, 17), (3, 18), (3, 19), (3, 20) |
| | | (4, 3), (5, 3), (6, 3), (7, 3), (8, 3), (9, 3), (10, 3), |
| | | (11, 3), (12, 3), (13, 3), (14, 3), (15, 3), (16, 3), |
| | | (17, 3), (18, 3), (19, 3), (20, 3) |
| 1-5 | $R^A$-5 | $R^{7a}$ = |
| 1-7 | $R^A$-7 | (1), (2), (3), (4), (5), (6), (7), (8), (9), (10), |
| 1-8 | or | (11), (12), (13), (14), (15), (16), (17), (18), (19) or |
| | $R^A$-8 | (20) |
| 1-9 | $R^A$-9 | |

[Chemical formula 22]

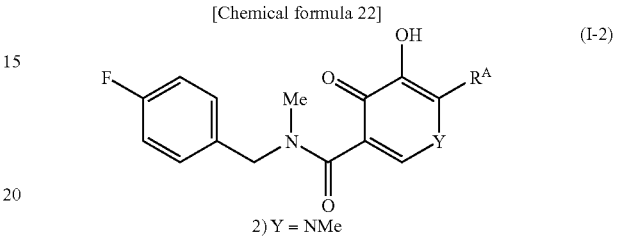

(I-2)

2) Y = NMe

| 1-1 | $R^A$-1 | $R^{6a}$ = |
|---|---|---|
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}$ = |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}$ = |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}$ = |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 23]

(I-2)

3) Y = NPh

| 1-1 | $R^A$-1 | $R^{6a}$= |
|---|---|---|
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}$ = |
| | | (1, 1), (1, 2), (1, 3), (1, 4), (1, 5), (1, 6), (1, 7), (1, 8), |

-continued

| No | $R^A$ | $R^6, R^7$ |
|---|---|---|
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 24] (I-2)

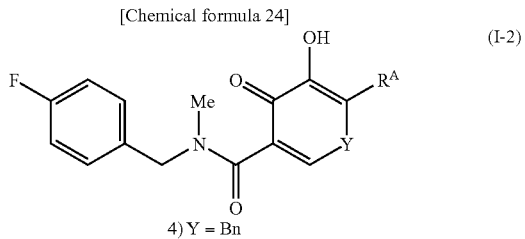

4) Y = Bn

| 1-1 | $R^A$-1 | $R^{6a}=$ |
|---|---|---|
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |

-continued

| No | $R^A$ | $R^6, R^7$ |
|---|---|---|
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 25] (I-2)

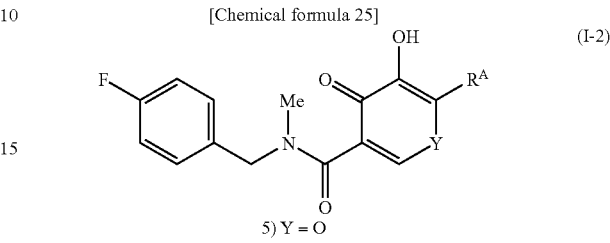

5) Y = O

| 1-1 | $R^A$-1 | $R^{6a}=$ |
|---|---|---|
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20),, |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

| No | $R^A$ | $R^6, R^7$ |
|---|---|---|

[Chemical formula 26] (I-3)

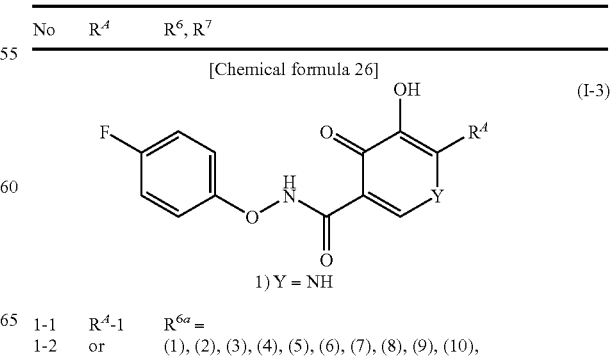

1) Y = NH

| 1-1 | $R^A$-1 | $R^{6a}=$ |
|---|---|---|
| 1-2 | or | (1), (2), (3), (4), (5), (6), (7), (8), (9), (10), |

| No | $R^A$ | $R^6, R^7$ |
|---|---|---|
| | $R^A$-2 | (11), (12), (13), (14) or (15) |
| 1-3 | $R^A$-3 | $R^{6a}, R^{6b} =$ |
| | | (1, 1), (1, 2), (1, 3), (1, 4), (1, 5), (1, 6), (1, 7), |
| | | (1, 8), (1, 9), (1, 10), (1, 11), (1, 12), (1, 13), |
| | | (1, 14), (1, 15) |
| | | (2, 2), (2, 3), (2, 4), (2, 5), (2, 6), (2, 7), (2, 8), |
| | | (2, 9), (2, 10), (2, 11), (2, 12), (2, 13), (2, 14), |
| | | (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4,10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b} =$ |
| 1-6 | $R^A$-6 | (1, 1), (1, 2), (1, 3), (1, 4), (1, 5), (1, 6), (1, 7), |
| 1-10 | $R^A$-10 | (1, 8), (1, 9), (1, 10), (1, 11), (1, 12), (1, 13), |
| 1-11 | or | (1, 14), (1, 15), (1, 16), (1, 17), (1, 18), (1, 19), |
| | $R^A$-11 | (1, 20), |
| | | (2, 1), (3, 1), (4, 1), (5, 1), (6, 1), (7, 1), (8, 1), |
| | | (9, 1), (10, 1), (11, 1), (12, 1), (13, 1), (14, 1), |
| | | (15, 1), (16, 1), (17, 1), (18, 1), (19, 1), (20, 1), |
| | | (2, 2), (2, 3), (2, 4), (2, 5), (2, 6), (2, 7), (2, 2), |
| | | (2, 9), (2, 10), (2, 11), (2, 12), (2, 13), (2, 8), |
| | | (2, 15), (2, 16), (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (3, 16), (3, 17), (3, 18), (3, 19), (3, 20) |
| | | (4, 3), (5, 3), (6, 3), (7, 3), (8, 3), (9, 3), (10, 3), |
| | | (11, 3), (12, 3), (13, 3), (14, 3), (15, 3), (16, 3), |
| | | (17, 3), (18, 3), (19, 3), (20, 3) |
| 1-5 | $R^A$-5 | $R^{7a} =$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 27]

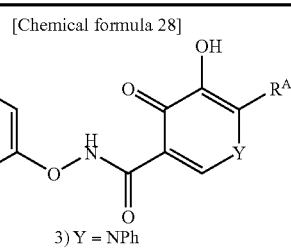

2) Y = NMe

| 1-1 | $R^A$-1 | $R^{6a} =$ |
|---|---|---|
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b} =$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b} =$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20), |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a} =$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 28]

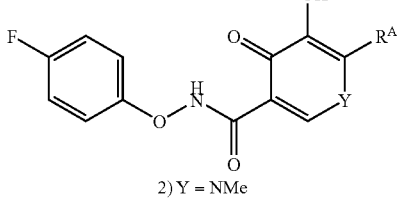

3) Y = NPh

| 1-1 | $R^A$-1 | $R^{6a} =$ |
|---|---|---|
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b} =$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b} =$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20), |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a} =$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 29]

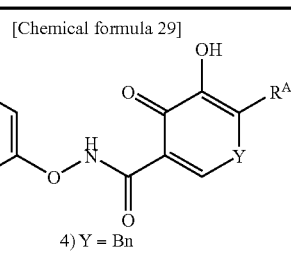

4) Y = Bn

| 1-1 | $R^A$-1 | $R^{6a} =$ |
|---|---|---|
| 1-2 | or | (1), (2), (3), (4), (5), (6), (7), (8), (9), (10), |

-continued

| No | $R^A$ | $R^6, R^7$ |
|---|---|---|
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20), |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

[Chemical formula 30]

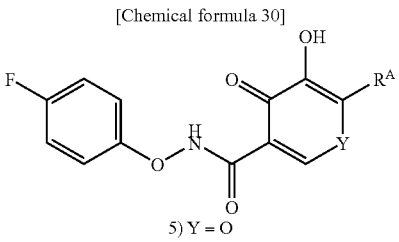

(I-3)

5) Y = O

| No | $R^A$ | $R^6, R^7$ |
|---|---|---|
| 1-1 | $R^A$-1 | $R^{6a}=$ |
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), (1, 8), |
| | | (1, 9), (1, 10), (1, 11), (1, 12), (1, 13), (1, 14), (1, 15) |
| | | (2, 2), (2, 3), (2, 4), (2, 5), (2, 6), (2, 7), (2, 8), (2, 9), |
| | | (2, 10), (2, 11), (2, 12), (2, 13), (2, 14), (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20), |
| | $R^A$-11 | (2, 1), (3, 1), (4, 1), (5, 1), (6, 1), (7, 1), (8, 1), (9, 1), |
| | | (10, 1), (11, 1), (12, 1), (13, 1), (14, 1), (15, 1), |
| | | (16, 1), (17, 1), (18, 1), (19, 1), (20, 1), |
| | | (2, 2), (2, 3), (2, 4), (2, 5), (2, 6), (2, 7), (2, 8), (2, 9), |
| | | (2, 10), (2, 11), (2, 12), (2, 13), (2, 14) (2, 15), (2, 16), |
| | | (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), |
| | | (3, 15), (3, 16), (3, 17), (3, 18), (3, 19), (3, 20) |

-continued

| No | $R^A$ | $R^6, R^7$ |
|---|---|---|
| | | (4, 3), (5, 3), (6, 3), (7, 3), (8, 3), (9, 3), |
| | | (10, 3), (11, 3), (12, 3), (13, 3), (14, 3), (15, 3), |
| | | (16, 3), (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

| No | $R^A$ | $R^6, R^7$ |
|---|---|---|

[Chemical formula 31]

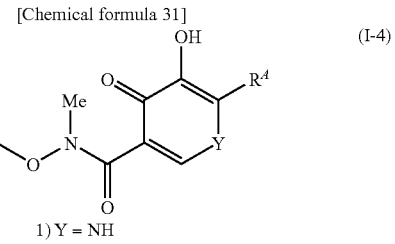

(I-4)

1) Y = NH

| | | |
|---|---|---|
| 1-1 | $R^A$-1 | $R^{6a}=$ |
| 1-2 | or | (1), (2), (3), (4), (5), (6), (7), (8), (9), (10), |
| | $R^A$-2 | (11), (12), (13), (14) or (15) |
| 1-3 | $R^A$-3 | $R^{6a}, R^{6b}=$ |
| | | (1, 1), (1, 2), (1, 3), (1, 4), (1, 5), (1, 6), (1, 7), |
| | | (1, 8), (1, 9), (1, 10), (1, 11), (1, 12), (1, 13), |
| | | (1, 14), (1, 15) |
| | | (2, 2), (2, 3), (2, 4), (2, 5), (2, 6), (2, 7), (2, 8), |
| | | (2, 9), (2, 10), (2, 11), (2, 12), (2, 13), (2, 14), |
| | | (2, 15) |
| | | (3, 3), (3, 4), (3, 5), (3, 6), (3, 7), (3, 8), (3, 9), |
| | | (3, 10), (3, 11), (3, 12), (3, 13), (3, 14), (3, 15) |
| | | (4, 4), (4, 5), (4, 6), (4, 7), (4, 8), (4, 9), (4, 10), |
| | | (4, 11), (4, 12), (4, 13), (4, 14), (4, 15) |
| | | (5, 5), (6, 6), (7, 7), (8, 8), or (9, 9) |
| 1-4 | $R^A$-4 | $R^{7a}, R^{7b}=$ |
| 1-6 | $R^A$-6 | (1, 1), (1, 2), (1, 3), (1, 4), (1, 5), (1, 6), (1, 7), |
| 1-10 | $R^A$-10 | (1, 8), (1, 9), (1, 10), (1, 11), (1, 12), (1, 13), |
| 1-11 | or | (1, 14), (1, 15), (1, 16), (1, 17), (1, 18), (1,19) |
| | $R^A$-11 | (1, 20), |
| | | (2, 1), (3, 1), (4, 1), (5, 1), (6, 1), (7, 1), (8, 1), |
| | | (9, 1), (10, 1), (11, 1), (12, 1), (13, 1), (14, 1), |
| | | (15, 1), (16, 1), (17, 1), (18, 1), (19, 1), (20, 1), |
| | | (2, 2), (2, 3), (2, 4), (2, 5), (2, 6), (2, 7), (2, 8), |
| | | (2, 9), (2, 10), (2, 11), (2, 12), (2, 13), (2, 14), |
| | | (2, 15), (2, 16), (2, 17), (2, 18), (2, 19), (2, 20), |
| | | (3, 2), (4, 2), (5, 2), (6, 2), (7, 2), (8, 2), (9, 2), |
| | | (10, 2), (11, 2), (12, 2), (13, 21), (14, 2), (15, 2), |
| | | (16, 2), (17, 2), (18, 2), (19, 2), (20, 2) |
| | | (3, 3), (3, 4), (3, 5), (3, 6), (3, 7), (3, 8), (3, 9), |
| | | (3, 10), (3, 11), (3, 12), (3, 13), (3, 14), (3, 15), |
| | | (3, 16), (3, 17), (3, 18), (3, 19), (3, 20) |
| | | (4, 3), (5, 3), (6, 3), (7, 3), (8, 3), (9, 3), (10, 3), |
| | | (11, 3), (12, 3), (13, 3), (14, 3), (15, 3), (16, 3), |
| | | (17, 3), (18, 3), (19, 3), (20, 3) |
| 1-5 | $R^A$-5 | $R^{7a}=$ |
| 1-7 | $R^A$-7 | (1), (2), (3), (4), (5), (6), (7), (8), (9), (10), |
| 1-8 | or | (11), (12), (13), (14), (15), (16), (17), (18), (19) |
| | $R^A$-8 | or (20) |
| 1-9 | $R^A$-9 | |

-continued

| No | $R^A$ | $R^6, R^7$ |
|---|---|---|

[Chemical formula 32] (I-4)

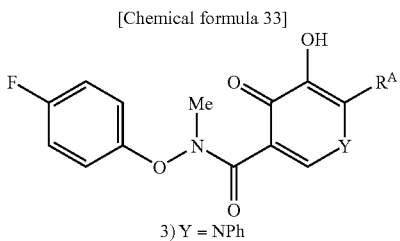

2) Y = NMe

| No | $R^A$ | $R^6, R^7$ |
|---|---|---|
| 1-1<br>1-2 | $R^A$-1 or<br>$R^A$-2 | $R^{6a}=$<br>(1), (2), (3), (4), (5), (6), (7), (8), (9), (10),<br>(11), (12), (13), (14) or (15) |
| 1-3 | $R^A$-3 | $R^{6a}, R^{6b}=$<br>(1, 1), (1, 2), (1, 3), (1, 4), (1, 5), (1, 6), (1, 7), (1, 8),<br>(1, 9), (1, 10), (1, 11), (1, 12), (1, 13), (1, 14), (1, 15)<br>(2, 2), (2, 3), (2, 4), (2, 5), (2, 6), (2, 7), (2, 8), (2, 9),<br>(2, 10), (2, 11), (2, 12), (2, 13), (2, 14), (2, 15)<br>(3, 3), (3, 4), (3, 5), (3, 6), (3, 7), (3, 8), (3, 9),<br>(3, 10), (3, 11), (3, 12), (3, 13), (3, 14), (3, 15)<br>(4, 4), (4, 5), (4, 6), (4, 7), (4, 8), (4, 9), (4, 10),<br>(4, 11), (4, 12), (4, 13), (4, 14), (4, 15)<br>(5, 5), (6, 6), (7, 7), (8, 8), or (9, 9) |
| 1-4<br>1-6<br>1-10<br>1-11 | $R^A$-4<br>$R^A$-6<br>$R^A$-10 or<br>$R^A$-11 | $R^{7a}, R^{7b}=$<br>(1, 1), (1, 2), (1, 3), (1, 4), (1, 5), (1, 6), (1, 7), (1, 8),<br>(1, 9), (1, 10), (1, 11) (1, 12), (1, 13), (1, 14), (1, 15),<br>(1, 16), (1, 17), (1, 18), (1, 19) (1, 20),<br>(2, 1), (3, 1), (4, 1), (5, 1), (6, 1), (7, 1), (8, 1), (9, 1),<br>(10, 1), (11, 1), (12, 1), (13, 1), (14, 1), (15, 1),<br>(16, 1), (17, 1), (18, 1), (19, 1), (20, 1),<br>(2, 2), (2, 3), (2, 4), (2, 5), (2, 6), (2, 7), (2, 8), (2, 9),<br>(2, 10), (2, 11), (2, 12), (2, 13), (2, 14) (2, 15), (2, 16),<br>(2, 17), (2, 18), (2, 19), (2, 20),<br>(3, 2), (4, 2), (5, 2), (6, 2), (7, 2), (8, 2), (9, 2),<br>(10, 2), (11, 2), (12, 2), (13, 21), (14, 2), (15, 2),<br>(16, 2), (17, 2), (18, 2), (19, 2), (20, 2)<br>(3, 3), (3, 4), (3, 5), (3, 6), (3, 7), (3, 8), (3, 9),<br>(3, 10), (3, 11), (3, 12), (3, 13), (3, 14),<br>(3, 15), (3, 16), (3, 17), (3, 18), (3, 19), (3, 20)<br>(4, 3), (5, 3), (6, 3), (7, 3), (8, 3), (9, 3),<br>(10, 3), (11, 3), (12, 3), (13, 3), (14, 3), (15, 3),<br>(16, 3), (17, 3), (18, 3), (19, 3), (20, 3) |
| 1-5<br>1-7<br>1-8<br>1-9 | $R^A$-5<br>$R^A$-7 or<br>$R^A$-8<br>$R^A$-9 | $R^{7a}=$<br>(1), (2), (3), (4), (5), (6), (7), (8), (9), (10),<br>(11), (12), (13), (14), (15), (16), (17), (18), (19)<br>or (20) |

[Chemical formula 33] (I-4)

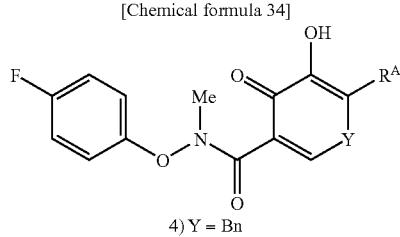

3) Y = NPh

| 1-1<br>1-2 | $R^A$-1 or<br>$R^A$-2 | $R^{6a}=$<br>(1), (2), (3), (4), (5), (6), (7), (8), (9), (10),<br>(11), (12), (13), (14) or (15) |
| 1-3 | $R^A$-3 | $R^{6a}, R^{6b}=$<br>(1, 1), (1, 2), (1, 3), (1, 4), (1, 5), (1, 6), (1, 7), (1, 8),<br>(1, 9), (1, 10), (1, 11), (1, 12), (1, 13), (1, 14), (1, 15)<br>(2, 2), (2, 3), (2, 4), (2, 5), (2, 6), (2, 7), (2, 8), (2, 9),<br>(2, 10), (2, 11), (2, 12), (2, 13), (2, 14), (2, 15)<br>(3, 3), (3, 4), (3, 5), (3, 6), (3, 7), (3, 8), (3, 9),<br>(3, 10), (3, 11), (3, 12), (3, 13), (3, 14), (3, 15)<br>(4, 4), (4, 5), (4, 6), (4, 7), (4, 8), (4, 9), (4, 10),<br>(4, 11), (4, 12), (4, 13), (4, 14), (4, 15)<br>(5, 5), (6, 6), (7, 7), (8, 8), or (9, 9) |
| 1-4<br>1-6 | $R^A$-4<br>$R^A$-6 | $R^{7a}, R^{7b}=$<br>(1, 1), (1, 2), (1, 3), (1, 4), (1, 5), (1, 6), (1, 7), (1, 8), |

-continued

| No | $R^A$ | $R^6, R^7$ |
|---|---|---|
| 1-10<br>1-11 | $R^A$-10 or<br>$R^A$-11 | (1, 9), (1, 10), (1, 11) (1, 12), (1, 13), (1, 14), (1, 15),<br>(1, 16), (1, 17), (1, 18), (1, 19) (1, 20),<br>(2, 1), (3, 1), (4, 1), (5, 1), (6, 1), (7, 1), (8, 1), (9, 1),<br>(10, 1), (11, 1), (12, 1), (13, 1), (14, 1), (15, 1),<br>(16, 1), (17, 1), (18, 1), (19, 1), (20, 1),<br>(2, 2), (2, 3), (2, 4), (2, 5), (2, 6), (2, 7), (2, 8), (2, 9),<br>(2, 10), (2, 11), (2, 12), (2, 13), (2, 14) (2, 15), (2, 16),<br>(2, 17), (2, 18), (2, 19), (2, 20),<br>(3, 2), (4, 2), (5, 2), (6, 2), (7, 2), (8, 2), (9, 2),<br>(10, 2), (11, 2), (12, 2), (13, 21), (14, 2), (15, 2),<br>(16, 2), (17, 2), (18, 2), (19, 2), (20, 2)<br>(3, 3), (3, 4), (3, 5), (3, 6), (3, 7), (3, 8), (3, 9),<br>(3, 10), (3, 11), (3, 12), (3, 13), (3, 14),<br>(3, 15), (3, 16), (3, 17), (3, 18), (3, 19), (3, 20)<br>(4, 3), (5, 3), (6, 3), (7, 3), (8, 3), (9, 3),<br>(10, 3), (11, 3), (12, 3), (13, 3), (14, 3), (15, 3),<br>(16, 3), (17, 3), (18, 3), (19, 3), (20, 3) |
| 1-5<br>1-7<br>1-8<br>1-9 | $R^A$-5<br>$R^A$-7 or<br>$R^A$-8<br>$R^A$-9 | $R^{7a}=$<br>(1), (2), (3), (4), (5), (6), (7), (8), (9), (10),<br>(11), (12), (13), (14), (15), (16), (17), (18), (19)<br>or (20) |

[Chemical formula 34] (I-5)

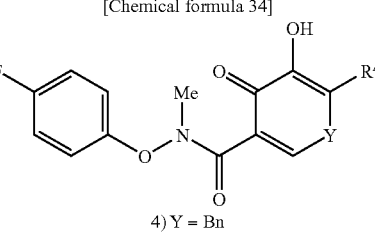

4) Y = Bn

| 1-1<br>1-2 | $R^A$-1 or<br>$R^A$-2 | $R^{6a}=$<br>(1), (2), (3), (4), (5), (6), (7), (8), (9), (10),<br>(11), (12), (13), (14) or (15) |
| 1-3 | $R^A$-3 | $R^{6a}, R^{6b}=$<br>(1, 1), (1, 2), (1, 3), (1, 4), (1, 5), (1, 6), (1, 7), (1, 8),<br>(1, 9), (1, 10), (1, 11), (1, 12), (1, 13), (1, 14), (1, 15)<br>(2, 2), (2, 3), (2, 4), (2, 5), (2, 6), (2, 7), (2, 8), (2, 9),<br>(2, 10), (2, 11), (2, 12), (2, 13), (2, 14), (2, 15)<br>(3, 3), (3, 4), (3, 5), (3, 6), (3, 7), (3, 8), (3, 9),<br>(3, 10), (3, 11), (3, 12), (3, 13), (3, 14), (3, 15)<br>(4, 4), (4, 5), (4, 6), (4, 7), (4, 8), (4, 9), (4, 10),<br>(4, 11), (4, 12), (4, 13), (4, 14), (4, 15)<br>(5, 5), (6, 6), (7, 7), (8, 8), or (9, 9) |
| 1-4<br>1-6<br>1-10<br>1-11 | $R^A$-4<br>$R^A$-6<br>$R^A$-10 or<br>$R^A$-11 | $R^{7a}, R^{7b}=$<br>(1, 1), (1, 2), (1, 3), (1, 4), (1, 5), (1, 6), (1, 7), (1, 8),<br>(1, 9), (1, 10), (1, 11) (1, 12), (1, 13), (1, 14), (1, 15),<br>(1, 16), (1, 17), (1, 18), (1, 19) (1, 20),<br>(2, 1), (3, 1), (4, 1), (5, 1), (6, 1), (7, 1), (8, 1), (9, 1),<br>(10, 1), (11, 1), (12, 1), (13, 1), (14, 1), (15, 1),<br>(16, 1), (17, 1), (18, 1), (19, 1), (20, 1),<br>(2, 2), (2, 3), (2, 4), (2, 5), (2, 6), (2, 7), (2, 8), (2, 9),<br>(2, 10), (2, 11), (2, 12), (2, 13), (2, 14) (2, 15), (2, 16),<br>(2, 17), (2, 18), (2, 19), (2, 20),<br>(3, 2), (4, 2), (5, 2), (6, 2), (7, 2), (8, 2), (9, 2),<br>(10, 2), (11, 2), (12, 2), (13, 21), (14, 2), (15, 2),<br>(16, 2), (17, 2), (18, 2), (19, 2), (20, 2)<br>(3, 3), (3, 4), (3, 5), (3, 6), (3, 7), (3, 8), (3, 9),<br>(3, 10), (3, 11), (3, 12), (3, 13), (3, 14),<br>(3, 15), (3, 16), (3, 17), (3, 18), (3, 19), (3, 20)<br>(4, 3), (5, 3), (6, 3), (7, 3), (8, 3), (9, 3),<br>(10, 3), (11, 3), (12, 3), (13, 3), (14, 3), (15, 3),<br>(16, 3), (17, 3), (18, 3), (19, 3), (20, 3) |
| 1-5<br>1-7<br>1-8<br>1-9 | $R^A$-5<br>$R^A$-7 or<br>$R^A$-8<br>$R^A$-9 | $R^{7a}=$<br>(1), (2), (3), (4), (5), (6), (7), (8), (9), (10),<br>(11), (12), (13), (14), (15), (16), (17), (18), (19)<br>or (20) |

| No | $R^A$ | $R^6, R^7$ |
|---|---|---|

[Chemical formula 35] (I-4)

5) Y = O

| | | |
|---|---|---|
| 1-1 | $R^A$-1 | $R^{6a}$ = |
| 1-2 | or | (1), (2), (3), (4), (5), (6), (7), (8), (9), (10), |
|  | $R^A$-2 | (11), (12), (13), (14) or (15) |
| 1-3 | $R^A$-3 | $R^{6a}, R^{6b}$ = |
|  |  | (1, 1), (1, 2), (1, 3), (1, 4), (1, 5), (1, 6), (1, 7), (1, 8), |
|  |  | (1, 9), (1, 10), (1, 11), (1, 12), (1, 13), (1, 14), (1, 15) |
|  |  | (2, 2), (2, 3), (2, 4), (2, 5), (2, 6), (2, 7), (2, 8), (2, 9), |
|  |  | (2, 10), (2, 11), (2, 12), (2, 13), (2, 14), (2, 15) |
|  |  | (3, 3), (3, 4), (3, 5), (3, 6), (3, 7), (3, 8), (3, 9), |
|  |  | (3, 10), (3, 11), (3, 12), (3, 13), (3, 14), (3, 15) |
|  |  | (4, 4), (4, 5), (4, 6), (4, 7), (4, 8), (4, 9), (4, 10), |
|  |  | (4, 11), (4, 12), (4, 13), (4, 14), (4, 15) |
|  |  | (5, 5), (6, 6), (7, 7), (8, 8), or (9, 9) |
| 1-4 | $R^A$-4 | $R^{7a}, R^{7b}$ = |
| 1-6 | $R^A$-6 | (1, 1), (1, 2), (1, 3), (1, 4), (1, 5), (1, 6), (1, 7), (1, 8), |
| 1-10 | $R^A$-10 | (1, 9), (1, 10), (1, 11) (1, 12), (1, 13), (1, 14), (1, 15), |
| 1-11 | or | (1, 16), (1, 17), (1, 18), (1, 19) (1, 20), |
|  | $R^A$-11 | (2, 1), (3, 1), (4, 1), (5, 1), (6, 1), (7, 1), (8, 1), (9, 1), |
|  |  | (10, 1), (11, 1), (12, 1), (13, 1), (14, 1), (15, 1), |
|  |  | (16, 1), (17, 1), (18, 1), (19, 1), (20, 1), |
|  |  | (2, 2), (2, 3), (2, 4), (2, 5), (2, 6), (2, 7), (2, 8), (2, 9), |
|  |  | (2, 10), (2, 11), (2, 12), (2, 13), (2, 14) (2, 15), (2, 16), |
|  |  | (2, 17), (2, 18), (2, 19), (2, 20), |
|  |  | (3, 2), (4, 2), (5, 2), (6, 2), (7, 2), (8, 2), (9, 2), |
|  |  | (10, 2), (11, 2), (12, 2), (13, 21), (14, 2), (15, 2), |
|  |  | (16, 2), (17, 2), (18, 2), (19, 2), (20, 2) |
|  |  | (3, 3), (3, 4), (3, 5), (3, 6), (3, 7), (3, 8), (3, 9), |
|  |  | (3, 10), (3, 11), (3, 12), (3, 13), (3, 14), |
|  |  | (3, 15), (3, 16), (3, 17), (3, 18), (3, 19), (3, 20) |
|  |  | (4, 3), (5, 3), (6, 3), (7, 3), (8, 3), (9, 3), |
|  |  | (10, 3), (11, 3), (12, 3), (13, 3), (14, 3), (15, 3), |
|  |  | (16, 3), (17, 3), (18, 3), (19, 3), (20, 3) |
| 1-5 | $R^A$-5 | $R^{7a}$ = |
| 1-7 | $R^A$-7 | (1), (2), (3), (4), (5), (6), (7), (8), (9), (10), |
| 1-8 | or | (11), (12), (13), (14), (15), (16), (17), (18), (19) |
|  | $R^A$-8 | or (20) |
| 1-9 | $R^A$-9 | |

The present invention further provides the following compounds. $R^A$, $R^{7a}$, and $R^{7b}$ are selected from the aforementioned group. $R^2$-X is selected from the following group. (1) hydrogen, (2) methyl, (3) ethyl, (4) n-propyl, (5) isopropyl., (6) 2-hydroxyethyl, (7) 2-methoxyethyl, (8) phenyl, (9) benzyl, (10) morpholine, (11) 1,1-dimethylhydrazine, (12) O-methylhydroxylamine

| No | $R^A$ | $R^7$ |
|---|---|---|

[Chemical formula 38] (I-5)

1) Y = NH, $R^2$—X = (1) to (12)

| | | |
|---|---|---|
| 1-5 | $R^A$-5 | $R^{7a}$ = (18), (19), (20) |
| 1-7 | $R^A$-7 | |
| 1-8 | $R^A$-8 | |
| 1-4 | $R^A$-4 | $R^{7a}, R^{7b}$ = (9, 1), (18, 1), (19, 1), (1, 9), (1, 18), |
| 1-6 | $R^A$-6 | (1, 19), (1, 20) |
| 1-10 | $R^A$-10 | |
| 1-11 | $R^A$-11 | |

[Chemical formula 39] (I-5)

2) Y = NMe, $R^2$-X = (1) to (12)

| | | |
|---|---|---|
| 1-5 | $R^A$-5 | $R^{7a}$ = (18), (19), (20) |
| 1-7 | $R^A$-7 | |
| 1-8 | $R^A$-8 | |
| 1-4 | $R^A$-4 | $R^{7a}, R^{7b}$ = (9, 1), (18, 1), (19, 1), (1, 9), (1, 18), |
| 1-6 | $R^A$-6 | (1, 19), (1, 20) |
| 1-10 | $R^A$-10 | |
| 1-11 | $R^A$-11 | |

[Chemical formula 40] (I-5)

3) Y = NPh, $R^2$-X = (1) to (12)

| | | |
|---|---|---|
| 1-5 | $R^A$-5 | $R^{7a}$ = (18), (19), (20) |
| 1-7 | $R^A$-7 | |
| 1-8 | $R^A$-8 | |
| 1-4 | $R^A$-4 | $R^{7a}, R^{7b}$ = (9, 1), (18, 1), (19, 1), (1, 9), (1, 18), |
| 1-6 | $R^A$-6 | (1, 19), (1, 20) |
| 1-10 | $R^A$-10 | |
| 1-11 | $R^A$-11 | |

[Chemical formula 41] (I-5)

4) Y = NPh, $R^2$-X = (1) to (12)

| | | |
|---|---|---|
| 1-5 | $R^A$-5 | $R^{7a}$ = (18), (19), (20) |
| 1-7 | $R^A$-7 | |
| 1-8 | $R^A$-8 | |
| 1-4 | $R^A$-4 | $R^{7a}, R^{7b}$ = (9, 1), (18, 1), (19, 1), (1, 9), (1, 18), |
| 1-6 | $R^A$-6 | (1, 19), (1, 20) |
| 1-10 | $R^A$-10 | |
| 1-11 | $R^A$-11 | |

[Chemical formula 42] (I-5)

5) Y = O, $R^2$-X = (1) to (12)

| | | |
|---|---|---|
| 1-5 | $R^A$-5 | $R^{7a}$ = (18), (19), (20) |
| 1-7 | $R^A$-7 | |
| 1-8 | $R^A$-8 | |
| 1-4 | $R^A$-4 | $R^{7a}, R^{7b}$ = (9, 1), (18, 1), (19, 1), (1, 9), (1, 18), |
| 1-6 | $R^A$-6 | (1, 19), (1, 20) |
| 1-10 | $R^A$-10 | |
| 1-11 | $R^A$-11 | |

[Chemical formula 43]

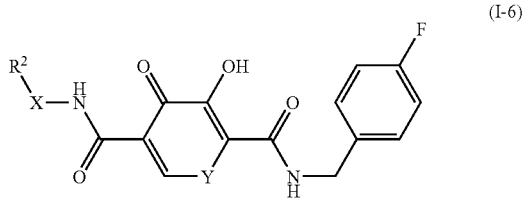
(I-6)

Y=NH, NMe, NPh, NBn, O, S
$R^2$-X=(1), (2), (3), (4), (5), (6), (7), (8), (9), (10), (11), or (12)

[Chemical formula 44]

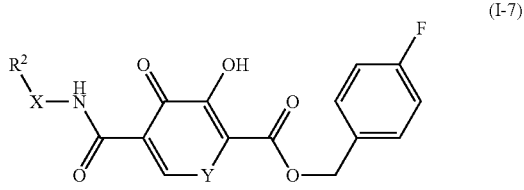
(I-7)

Y=NH, NMe, NPh, NBn, O, S
$R^2$-X=(1), (2), (3), (4), (5), (6), (7), (8), (9), (10), (11), or (12)

Experimental Example 1

The HIV integrase inhibitory activity was examined based on an assay method shown below.

(1) Preparation of DNA Solution

According to the same method as the method described in Test Example 1 of WO 2004/024693, a substrate DNA solution (2 pmol/μl) and a target DNA solution (5 pmol/μl) were prepared. Each target DNA solution was used after it was boiled, and a temperature was slowly lowered to anneal complementary chains. Each sequence of a substrate DNA and a target DNA is as described in the same Test Example.

(2) Measurement of Inhibition Rate ($IC_{50}$ Value)

Streptavidin (manufactured by Vector Laboratories) was dissolved in a 0. 1M carbonate buffer (composition: 90 mM $Na_2CO_3$, 10 mM $NaHCO_3$ )to a concentration of 40 μg/ml. Each 50 μl of this solution was added to a well of an immunoplate (manufactured by NUNC), and this was allowed to stand at 4° C. overnight to perform adsorption. Then, each well was washed with, a phosphate buffer (composition: 13.7 mM NaCl, 0.27 mM KCl, 0.43 mM. $Na_2HPO_4$, 0.14 mM $KH_2PO_4$) two times, 300 μl of a phosphate buffer containing 1% skim milk was added, and blocking was performed for 30 minutes. Further, each well was washed with a phosphate buffer two times, 50 μl of a substrate DNA solution (2 pmol/μl) was added, adsorption was performed at room temperature for 30 minutes under shaking, and this was washed with a phosphate buffer two times and, then, distilled water once.

Then, to each well prepared by the aforementioned method was added 51 μl of a reaction solution prepared from 12 μl of a buffer (composition: 150 mM MOPS (pH7.2), 75 mM $MnCl_2$, 50 mM 2-mercaptoethanol, 25% glycerol, 500 μg/ml bovine serum albumin-fraction V)and 39 μl of distilled water. Then, 9 μl of an integrase solution (30 pmol) was added, followed by mixing well. To a well as a negative control (NC) was added 9 μl of a diluent (composition: 20 mM MOPS (pH 7.2), 400 mM potassium glutamete, 1 mM EDTA, 0.1% NP-40, 20% glycerol, 1 mM DTT, 4 M urea), and this was mixed well using a plate mixer.

The plate was incubated at, 30° C. for 60 minutes, and the reaction solution was discarded, followed by washing with 250 μl of washing buffer (composition: 150 mM MOPS (pH 7.2), 50 mM 2-mercaptoethanol, 25% glycerol., 500 μg/ml bovine serum albumin-fraction V) three times.

Then, to each well was added 53 μl of a reaction solution prepared from 12 μl of a buffer (composition: 150 mM MOPS (pH 7.2), 75 mM $MgCl_2$, 50 mM 2-mercaptoethanol, 25% glycerol, 500 μg/ml bovine serum albumin-fraction V)and 41 μl of distilled water. Further, 6 μl of a solution of a test compound in DMSO was added to each well, and 6 μl of DMSO was added to a well as a positive control (PC), followed by mixing well using a plate mixer. After the plate was incubated at 30° C. for 30 minutes, 1 μl of a target DNA (5 pmol/μl) was added, and this was mixed well using a plate mixer.

Each plate was incubated at 30° C. for 10 minutes, and the reaction solution was discarded, followed by washing with a phosphate buffer two times. Then, an alkaline phosphatase-labeled anti-digoxigenin antibody (sheep Fab fragment: manufactured by Boehringer) was diluted 2000-fold with an antibody diluent, 100 μl was added to allow them to be bound at 30° C. for 1 hour, and this was washed sequentially with a phosphate buffer containing 0.05% Tween20 two times, and a phosphate buffer once. Then, 150 μl of an alkaline phosphatase-coloring buffer (composition: 10 mM paranitrophenyl phosphate (manufactured by Vector Laboratories), 5 mM $MgCl_2$, 100 mM NaCl, 100 mM Tris-hydrochloric acid (pH 9.5)) was added to perform a reaction at 30° C. for 2 hours, 50 μl of a 1N NaOH solution was added to stop the reaction, an absorbance (OD 405 nm) of each well was measured, and an inhibition rate ($IC_{50}$) was obtained according to the following calculation equation. Inhibition rate (%)=100[1−{(C abs.−NC abs.)/(PC abs.−NC abs.)}]

C abs.; absorbance of well of compound

NC abs.: absorbance of NC

PC abs.: absorbance of PC

Results of the above experiment are shown below.

TABLE 1

| Example (compound No.) | Integrase inhibitory activity ($IC_{50}$, ng/ml) |
| --- | --- |
| A-1 (A-1a) | 6.4 |
| A-3 (A-3) | 3.1 |

The present compound exhibited the strong integrase inhibitory activity against HIV.

Formulation Examples

The term "active ingredient" means the present compound, a tautomer thereof, a prodrug thereof, a pharmaceutically acceptable salt thereof, or a solvate thereof.

Formulation Example 1

A hard gelatin capsule is produced using the following ingredients:

|  | Dose (mg/capsule) |
| --- | --- |
| Active ingredient | 250 |
| Starch, dried | 200 |
| Magnesium stearate | 10 |
| Total | 460 mg |

Formulation Example 2

A tablet is produced using the following ingredients:

|  | Dose (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

Ingredients are mixed, and compressed to obtain tablets, each having a weight of 665 mg.

The invention claimed is:

1. A compound represented by the formula:

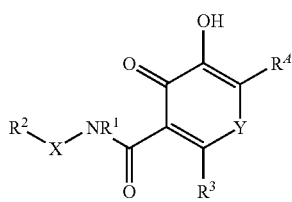

[chemical formula 1]

(I)

wherein
Y is NH;
$R^4$ is 1) a group represented by the formula: —$COR^5$, wherein $R^5$ is a group selected from a substituent group A, wherein substituent group A is hydrogen, hydroxy, optionally substituted lower alkyl, optionally substituted lower alkoxy, optionally substituted cycloalkyl, optionally substituted cycloalkyloxy, optionally substituted amino, optionally substituted aminooxy, optionally substituted heterocyclic group, optionally substituted heterocyclic oxy, optionally substituted aryl, optionally substituted aryloxy, optionally substituted aralkyl, optionally substituted aralkyloxy, formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, or optionally substituted arylcarbonyl;

or 2) a group represented by the formula:

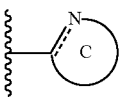

[chemical formula 2]

wherein a C ring is an optionally substituted nitrogen-containing aromatic heterocycle in which, among atoms adjacent to an atom having a bond, at least one atom is an unsubstituted nitrogen atom, and a broken line represents the presence or the absence of a bond;

$R^1$ is hydrogen or lower alkyl;

X is a single bond, a hetero atom group selected from O, S, SO, $SO_2$ and NH, or lower alkylene or lower alkenylene in which the hetero atom group may intervene;

$R^2$ is a group selected from the substituent group A;

$R^3$ is hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl;

or a pharmaceutically acceptable salt thereof.

2. The compound according to claim 1, or a pharmaceutically acceptable salt thereof, wherein $R^4$ is —$COR^5$, wherein $R^5$ is as defined above.

3. The compound according to claim 1, or a pharmaceutically acceptable salt thereof, wherein $R^4$ is —$COR^5$, wherein $R^5$ is hydrogen, hydroxy, optionally substituted lower alkyl, optionally substituted lower alkoxy, optionally substituted phenyl, optionally substituted benzyl, optionally substituted heterocyclic group or optionally substituted amino.

4. The compound according to claim 1, or a pharmaceutically acceptable salt thereof, wherein $R^4$ is —$COR^5$, wherein $R^5$ is hydrogen, hydroxy, lower alkyl, lower alkoxy, or optionally substituted amino.

5. The compound according to claim 1, or a pharmaceutically acceptable salt thereof, wherein $R^4$ is a group represented by the formula:

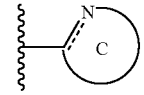

[chemical formula 3]

wherein a C ring is optionally substituted nitrogen-containing aromatic heterocycle in which, among atoms adjacent to an atom having a bond, at least one atom is an unsubstituted nitrogen atom, and a broken line represents the presence or the absence of a bond.

6. The compound according to claim 1, or a pharmaceutically acceptable salt thereof, wherein $R^4$ is an optionally substituted nitrogen-containing aromatic heterocyclic group which is any one of the following groups:

[chemical formula 4]
(C-1) 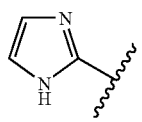
(C-2) 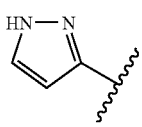
(C-3) 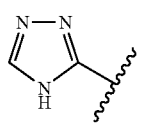
(C-4) 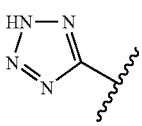
(C-5) 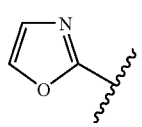
(C-6) 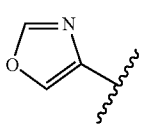
(C-7) 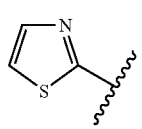
(C-8) 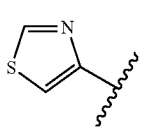
(C-9) 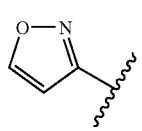
(C-10) 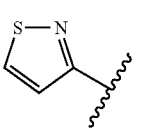
(C-11) 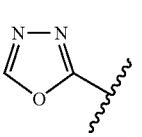
(C-12) 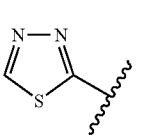
(C-13) 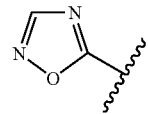
(C-14) 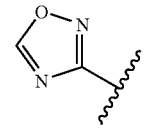
(C-15) 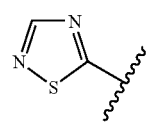
(C-16) 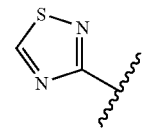
(C-17) 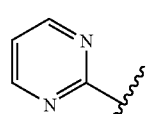
(C-18) 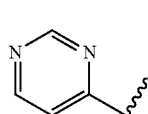
(C-19) 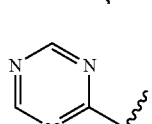
(C-20) 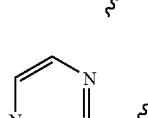
(C-21) 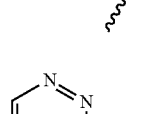
(C-22) 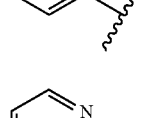
7. The compound according to claim 1, or a pharmaceutically acceptable salt thereof, wherein $R^A$ is an optionally substituted nitrogen-containing aromatic heterocyclic group which is any one of the following groups:

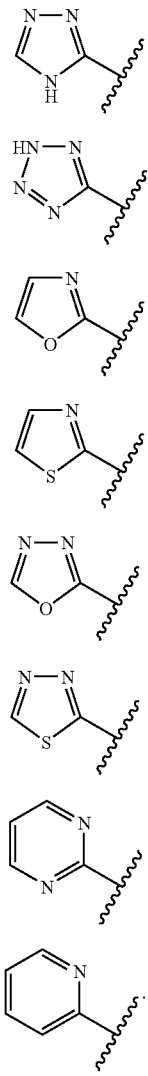

(C-3)
(C-4)
(C-5)
(C-7)
(C-11)
(C-12)
(C-17)
(C-22)

8. The compound according to claim 1, or a pharmaceutically acceptable salt thereof, wherein $R^1$ is hydrogen or methyl.

9. The compound according to the claim 1, or a pharmaceutically acceptable salt thereof, wherein X is lower alkylene or O; $R^2$ is optionally substituted phenyl.

10. The compound according to claim 1, or a pharmaceutically acceptable salt thereof, wherein $R^3$ is hydrogen, hydroxy, optionally substituted lower alkoxy, or optionally substituted amino.

11. The compound according to claim 1, or a pharmaceutically acceptable salt thereof, wherein $R^3$ is hydrogen.

12. The compound according to claim 1, or a pharmaceutically acceptable salt thereof, wherein $R^1$ is hydrogen or methyl; X is lower alkylene or O; $R^2$ is optionally substituted phenyl; $R^3$ is hydrogen.

13. The compound according to claim 1, or a pharmaceutically acceptable salt thereof, wherein $R^1$ is hydrogen or methyl; X is methylene or O; $R^2$ is phenyl optionally substituted with halogen; $R^3$ is hydrogen.

14. A pharmaceutical composition, comprising a compound as defined in claim 1, or a pharmaceutically acceptable salt thereof; and a pharmaceutically acceptable carrier or diluent.

15. An anti-HIV agent, comprising a compound as defined in claim 1, or a pharmaceutically acceptable salt thereof; and a pharmaceutically acceptable carrier or diluent.

16. A compound represented by the formula:

[chemical formula 6]

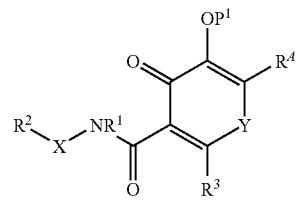

(I')

wherein
$P^1$ is a hydroxy protecting group;
Y is $NH^4$;
$R^A$ is 1) a group represented by the formula: —$COR^5$, wherein $R^5$ is a group selected from a substituent group A, wherein substituent group A is hydrogen, hydroxy, optionally substituted lower alkyl, optionally substituted lower alkoxy, optionally substituted cycloalkyl, optionally substituted cycloalkyloxy, optionally substituted amino, optionally substituted aminooxy, optionally substituted heterocyclic group, optionally substituted heterocyclic oxy, optionally substituted aryl, optionally substituted aryloxy, optionally substituted aralkyl, optionally substituted aralkyloxy, formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, or optionally substituted arylcarbonyl;
or 2) a group represented by the formula:

[chemical formula 7]

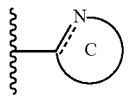

wherein a C ring is an optionally substituted nitrogen-containing aromatic heterocycle in which, among atoms adjacent to an atom having a bond, at least one atom is an unsaturated nitrogen atom, and a broken line represents the presence or the absence of a bond;
$R^1$ is hydrogen or lower alkyl;
X is a single bond, a hetero atom group selected from O, S, SO, $SO_2$ and NH, or lower alkylene or lower alkenylene in which the hetero atom group may intervene;
$R^2$ is a group selected from the substituent group A;
$R^3$ is hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl;

or a pharmaceutically acceptable salt thereof.

17. A compound represented by the formula:

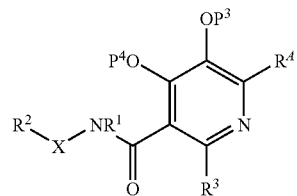

(I")

wherein
P³ is hydrogen or a hydroxy protecting group;
P⁴ is a hydroxy protecting group;
R⁴ is 1) a group represented by the formula: —COR⁵, wherein R⁵ is a group selected from a substitutent group A, wherein substituent group A is hydrogen, hydroxy, optionally substituted lower alkyl, optionally substituted lower alkoxy, optionally substituted cycloalkyl, optionally substituted cycloalkyloxy, optionally substituted amino, optionally substituted aminooxy, optionally substituted heterocyclic group, optionally substituted heterocyclic oxy, optionally substituted aryl, optionally substituted aryloxy, optionally substituted aralkyl, optionally substituted aralkyloxy, formyl, carboxy, optionally substituted lower alkanoyl, optionally substituted lower alkoxycarbonyl, optionally substituted carbamoyl, optionally substituted heterocyclic carbonyl, optionally substituted cycloalkylcarbonyl, or optionally substituted arylcarbonyl;

or 2) a group represented by the formula:

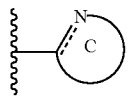

wherein a C ring is an optionally substituted nitrogen-containing aromatic heterocycle in which, among atoms adjacent to an atom having a bond, at least one atom is an unsubstituted nitrogen atom, and a broken line represents the presence or the absence of a bond;

R¹ is hydrogen or lower alkyl;
X is a single bond, a hetero atom group selected from O, S, SO, SO₂ and NH, or lower alkylene or lower alkenylene in which the hetero atom group may intervene;
R² is a group selected from the substituent group A;
R³ is hydrogen, halogen, hydroxy, optionally substituted lower alkyl, optionally substituted lower alkenyl, optionally substituted lower alkoxy, optionally substituted amino, optionally substituted lower alkylamino, optionally substituted cycloalkyl, optionally substituted cycloalkyl lower alkyl, optionally substituted aryl, optionally substituted aralkyl, optionally substituted heterocyclic group, or optionally substituted heterocyclic lower alkyl;

or a pharmaceutically acceptable salt thereof.

* * * * *